(12) United States Patent
Punyani et al.

(10) Patent No.: US 12,039,732 B2
(45) Date of Patent: Jul. 16, 2024

(54) DIGITAL IMAGING AND LEARNING SYSTEMS AND METHODS FOR ANALYZING PIXEL DATA OF A SCALP REGION OF A USERS SCALP TO GENERATE ONE OR MORE USER-SPECIFIC SCALP CLASSIFICATIONS

(71) Applicant: The Procter & Gamble Company, Cincinnati, OH (US)

(72) Inventors: Supriya Punyani, Singapore (SG); Vandana Reddy Padala, Singapore (SG)

(73) Assignee: The Procter & Gamble Company, Cincinnati, OH (US)

( * ) Notice: Subject to any disclaimer, the term of this patent is extended or adjusted under 35 U.S.C. 154(b) by 514 days.

(21) Appl. No.: 17/230,121

(22) Filed: Apr. 14, 2021

(65) Prior Publication Data

US 2022/0335614 A1     Oct. 20, 2022

(51) Int. Cl.
*G06T 7/00* (2017.01)
*G06F 18/214* (2023.01)
(Continued)

(52) U.S. Cl.
CPC .......... *G06T 7/0016* (2013.01); *G06F 18/214* (2023.01); *G06F 18/24* (2023.01);
(Continued)

(58) Field of Classification Search
CPC ......... G06T 7/0016; G06T 2207/20081; G06T 2207/30088; G16H 20/30; G06N 20/00;
(Continued)

(56) References Cited

U.S. PATENT DOCUMENTS 2,946,725 A     7/1960   Norris
3,070,510 A    12/1962   Cooley
(Continued)

FOREIGN PATENT DOCUMENTS

CN      101916334 A    12/2010
CN      104586362 A     5/2015
(Continued)

OTHER PUBLICATIONS

"How C-Lab is Preparing for a Future Full of Potential—Part 1: C-Lab Inside", Samsung Newsroom, pp. 5, Jan. 2, 2020.
(Continued)

*Primary Examiner* — William D Titcomb
(74) *Attorney, Agent, or Firm* — David M. Weirich

(57) ABSTRACT

Digital imaging and learning systems and methods are described for analyzing pixel data of a scalp region of a user's scalp to generate one or more user-specific scalp classifications. A digital image of a user is received at an imaging application (app) and comprises pixel data of at least a portion of a scalp region of the user's scalp. A scalp based learning model, trained with pixel data of a plurality of training images depicting scalp regions of scalps of respective individuals, analyzes the image to determine at least one image classification of the user's scalp region. The imaging app generates, based on the at least one image classification, a user-specific scalp classification designed to address at least one feature identifiable within the pixel data comprising the at least the portion of a scalp region of the user's scalp.

28 Claims, 5 Drawing Sheets

(51) Int. Cl.
 *G06F 18/24* (2023.01)
 *G06N 20/00* (2019.01)
 *G06Q 10/0833* (2023.01)
 *G16H 20/30* (2018.01)

(52) U.S. Cl.
 CPC ......... *G06N 20/00* (2019.01); *G06Q 10/0833* (2013.01); *G16H 20/30* (2018.01); *G06T 2207/20081* (2013.01); *G06T 2207/30088* (2013.01); *G06V 2201/03* (2022.01)

(58) Field of Classification Search
 CPC ... G06F 18/24; G06F 18/214; G06Q 10/0833; G06V 2201/03
 USPC ......................................................... 382/128
 See application file for complete search history.

(56) References Cited

U.S. PATENT DOCUMENTS

| | | | |
|---|---|---|---|
| 3,429,963 A | 2/1969 | Shedlovsky | |
| 3,506,720 A | 4/1970 | Model et al. | |
| 3,535,421 A | 10/1970 | Briner | |
| 3,538,230 A | 11/1970 | Pader | |
| 3,678,154 A | 7/1972 | Widder | |
| 3,689,637 A | 9/1972 | Pader | |
| 3,696,191 A | 10/1972 | Weeks | |
| 3,711,604 A | 1/1973 | Colodney et al. | |
| 3,737,533 A | 6/1973 | Moon et al. | |
| 3,862,307 A | 1/1975 | Di Giulio | |
| 3,911,104 A | 10/1975 | Harrison | |
| 3,935,306 A | 1/1976 | Roberts et al. | |
| 3,959,458 A | 5/1976 | Agricola | |
| 3,988,443 A | 10/1976 | Ploger et al. | |
| 3,991,177 A | 11/1976 | Vidra et al. | |
| 4,040,858 A | 8/1977 | Wason | |
| 4,051,234 A | 9/1977 | Gieske | |
| 4,058,595 A | 11/1977 | Colodney | |
| 4,138,477 A | 2/1979 | Gaffar | |
| 4,154,815 A | 5/1979 | Pader | |
| 4,183,914 A | 1/1980 | Gaffar | |
| 4,304,766 A | 12/1981 | Chang | |
| 4,355,022 A | 10/1982 | Rabussay | |
| 4,590,066 A | 5/1986 | Parran, Jr. et al. | |
| 4,627,977 A | 12/1986 | Gaffar | |
| 4,661,341 A | 4/1987 | Benedict et al. | |
| 4,846,650 A | 7/1989 | Benedict et al. | |
| 4,877,603 A | 10/1989 | Degenhardt | |
| 4,980,153 A | 12/1990 | Jackson et al. | |
| 4,992,420 A | 2/1991 | Neeser | |
| 5,000,939 A | 3/1991 | Dring et al. | |
| 5,037,637 A | 8/1991 | Gaffar et al. | |
| 5,626,838 A | 5/1997 | Cavanaugh, Jr. | |
| 5,827,505 A | 10/1998 | Hughes et al. | |
| 5,939,052 A | 8/1999 | White, Jr. et al. | |
| 6,251,372 B1 | 6/2001 | Witt et al. | |
| 6,707,929 B2 | 3/2004 | Marapane | |
| 7,079,158 B2 | 7/2006 | Lambertsen | |
| 7,104,800 B2 | 9/2006 | Ortiz-Valero | |
| 7,435,794 B2 | 10/2008 | Lukyanov et al. | |
| 7,437,344 B2 | 10/2008 | Peyrelevade | |
| 7,964,579 B2 | 6/2011 | Mehta et al. | |
| 8,119,162 B2 | 2/2012 | Miksa | |
| 8,168,600 B2 | 5/2012 | Dokka | |
| 8,216,786 B2 | 7/2012 | Shiffman et al. | |
| 8,241,651 B2 | 8/2012 | Lahann | |
| 8,338,115 B2 | 12/2012 | Adler | |
| 8,360,973 B2 | 1/2013 | Bazin | |
| 8,484,155 B2 | 7/2013 | Yamaguchi | |
| 8,871,920 B2 | 10/2014 | Purschke | |
| 9,457,071 B2 | 10/2016 | Hide | |
| 9,504,306 B2 | 11/2016 | Miller et al. | |
| 9,518,265 B2 | 12/2016 | Hohlig | |
| 9,709,576 B2 | 7/2017 | Hide | |
| 9,732,348 B2 | 8/2017 | Cauchard | |
| 9,779,289 B2 | 10/2017 | Movellan et al. | |
| 9,902,961 B2 | 2/2018 | Dausse | |
| 9,976,145 B2 | 5/2018 | Jarosch | |
| 9,996,674 B2 | 6/2018 | Segman | |
| 10,001,496 B2 | 6/2018 | Jung | |
| 10,231,531 B2 | 3/2019 | Witchell | |
| 10,308,943 B2 | 6/2019 | Erickson et al. | |
| 10,650,289 B2 | 5/2020 | Szegedy | |
| 10,676,396 B2 | 6/2020 | Johannsmann et al. | |
| 10,796,480 B2 * | 10/2020 | Chen | G06V 40/166 |
| 10,994,919 B2 | 5/2021 | Hochberg et al. | |
| 11,016,094 B2 | 5/2021 | Gilboa-geffen | |
| 11,172,873 B2 * | 11/2021 | Purwar | G06N 3/045 |
| 11,373,420 B2 * | 6/2022 | Pham | H04L 9/3297 |
| 11,455,747 B2 * | 9/2022 | Robinson | G06T 7/0014 |
| 11,896,114 B2 | 2/2024 | Katzarov | |
| 2002/0065452 A1 | 5/2002 | Bazin | |
| 2002/0150287 A1 | 10/2002 | Kobayashi | |
| 2002/0183988 A1 | 12/2002 | Skaanning | |
| 2003/0013994 A1 * | 1/2003 | Rubinstenn | A61B 5/1034 |
| | | | 600/587 |
| 2003/0014324 A1 | 1/2003 | Donovan | |
| 2003/0063801 A1 | 4/2003 | Rubinstenn et al. | |
| 2003/0064356 A1 * | 4/2003 | Rubinstenn | A45D 44/005 |
| | | | 434/377 |
| 2003/0065256 A1 | 4/2003 | Rubinstein | |
| 2004/0236592 A1 | 11/2004 | Aleles | |
| 2006/0085274 A1 | 4/2006 | Sottery | |
| 2006/0149151 A1 | 7/2006 | Ladjevardi | |
| 2006/0178904 A1 | 8/2006 | Aghassian | |
| 2007/0012320 A1 | 1/2007 | De Lacharriere et al. | |
| 2007/0054261 A1 | 3/2007 | Sherman | |
| 2007/0058858 A1 | 3/2007 | Harville | |
| 2008/0097814 A1 | 4/2008 | Koustoumbardis | |
| 2008/0152600 A1 | 6/2008 | Huang et al. | |
| 2008/0216334 A1 | 9/2008 | Pak et al. | |
| 2010/0106679 A1 | 4/2010 | Yamaguchi | |
| 2010/0254581 A1 | 10/2010 | Neeser | |
| 2011/0016001 A1 | 1/2011 | Schieffelin | |
| 2012/0041282 A1 | 2/2012 | Nichol | |
| 2012/0190627 A1 | 7/2012 | Delattre | |
| 2012/0296343 A1 * | 11/2012 | Bodduluri | A61B 5/0077 |
| | | | 606/133 |
| 2012/0320191 A1 | 12/2012 | Meschkat | |
| 2013/0323242 A1 | 12/2013 | Everett | |
| 2013/0332451 A1 | 12/2013 | Camplejohn et al. | |
| 2014/0018634 A1 | 1/2014 | Baumann | |
| 2014/0028822 A1 | 1/2014 | Khadavi | |
| 2014/0081095 A1 | 3/2014 | Krishnan | |
| 2014/0216492 A1 | 8/2014 | Magri | |
| 2014/0378810 A1 | 12/2014 | Davis | |
| 2015/0045631 A1 | 2/2015 | Ademola | |
| 2015/0217465 A1 | 8/2015 | Krenik | |
| 2015/0329863 A1 | 11/2015 | Cauchard et al. | |
| 2015/0353933 A1 | 12/2015 | Miyakawa et al. | |
| 2016/0061602 A1 | 3/2016 | Fessi | |
| 2016/0326530 A1 | 11/2016 | Dausse et al. | |
| 2017/0004558 A1 | 1/2017 | Abramowitz | |
| 2017/0107515 A1 | 4/2017 | Eberly et al. | |
| 2017/0166894 A1 | 6/2017 | Demock et al. | |
| 2017/0216172 A1 * | 8/2017 | Carballada | A61K 8/37 |
| 2017/0270593 A1 | 9/2017 | Sherman | |
| 2017/0273639 A1 * | 9/2017 | Iscoe | G06N 20/00 |
| 2018/0040052 A1 | 2/2018 | Robinson | |
| 2018/0040053 A1 | 2/2018 | Robinson | |
| 2018/0113997 A1 | 4/2018 | Tanigawa et al. | |
| 2018/0116583 A1 | 5/2018 | Cook | |
| 2018/0140248 A1 | 5/2018 | Chandra | |
| 2018/0223285 A1 | 8/2018 | Hohlig | |
| 2018/0225673 A1 | 8/2018 | Dubey | |
| 2018/0235535 A1 | 8/2018 | Cook | |
| 2018/0247365 A1 | 8/2018 | Cook | |
| 2018/0253866 A1 | 9/2018 | Jain | |
| 2018/0318719 A1 | 11/2018 | Ma et al. | |
| 2018/0349979 A1 | 12/2018 | Robinson | |
| 2018/0369614 A1 | 12/2018 | Manneck et al. | |
| 2019/0035149 A1 * | 1/2019 | Chen | G06V 40/166 |
| 2019/0048348 A1 | 2/2019 | Velasquez | |
| 2019/0048349 A1 | 2/2019 | Velasquez et al. | |

(56) References Cited

U.S. PATENT DOCUMENTS

| | | | |
|---|---|---|---|
| 2019/0112593 | A1 | 4/2019 | Penner |
| 2019/0142338 | A1* | 5/2019 | Fang ............... G16H 20/40 600/408 |
| 2019/0170726 | A1 | 6/2019 | Tsuji et al. |
| 2019/0183232 | A1 | 6/2019 | Knuebel et al. |
| 2019/0197357 | A1* | 6/2019 | Anderson ............ G06N 5/04 |
| 2019/0209077 | A1 | 7/2019 | Charraud |
| 2019/0350514 | A1 | 11/2019 | Purwar |
| 2019/0355115 | A1* | 11/2019 | Niebauer ............ A61B 5/441 |
| 2019/0355119 | A1 | 11/2019 | Hu |
| 2020/0000697 | A1 | 1/2020 | Velasquez et al. |
| 2020/0002703 | A1 | 1/2020 | Velasquez |
| 2020/0055659 | A1 | 2/2020 | Hochberg |
| 2020/0196936 | A1 | 6/2020 | Blank |
| 2020/0221995 | A1 | 7/2020 | Mathiaszyk et al. |
| 2020/0286152 | A1 | 9/2020 | Thiagarajan et al. |
| 2020/0320748 | A1 | 10/2020 | Levinshtein et al. |
| 2020/0330353 | A1 | 10/2020 | Velasquez et al. |
| 2020/0348662 | A1* | 11/2020 | Cella ............... G05B 19/41865 |
| 2020/0367961 | A1 | 11/2020 | Podmore et al. |
| 2021/0059754 | A1 | 3/2021 | Kasprzak |
| 2021/0097595 | A1 | 4/2021 | Senior, III et al. |
| 2021/0106696 | A1 | 4/2021 | Dalma-weiszhausz et al. |
| 2021/0142890 | A1 | 5/2021 | Adiri et al. |
| 2021/0334561 | A1* | 10/2021 | Pham ............... G06F 16/2465 |
| 2022/0005189 | A1* | 1/2022 | Perrot ............... G06T 7/10 |
| 2022/0101577 | A1 | 3/2022 | Chakrabarty et al. |
| 2022/0121839 | A1 | 4/2022 | Tagra et al. |
| 2022/0164852 | A1* | 5/2022 | Punyani ............. G06V 10/56 |
| 2023/0196579 | A1* | 6/2023 | Knight ............. G06V 40/171 382/128 |

FOREIGN PATENT DOCUMENTS

| | | |
|---|---|---|
| CN | 105441213 A | 3/2016 |
| CN | 105956150 A | 9/2016 |
| DE | 102018207560 A1 | 11/2019 |
| EP | 2443960 A1 | 4/2012 |
| EP | 3627444 A1 | 3/2020 |
| FR | 3020465 A1 | 10/2015 |
| GB | 490384 A | 8/1938 |
| JP | 2000287953 A | 10/2000 |
| JP | 2002360545 A | 12/2002 |
| JP | 2004354207 A | 12/2004 |
| JP | 2009172023 A | 8/2009 |
| JP | 3163309 U | 9/2010 |
| JP | 2015111372 A | 6/2015 |
| JP | 2016077649 A | 5/2016 |
| JP | 2016200955 A | 12/2016 |
| JP | 2017009426 A | 1/2017 |
| JP | 6138696 B2 | 5/2017 |
| JP | 2018041434 A | 3/2018 |
| JP | 2019212073 A | 12/2019 |
| JP | 6647438 B1 | 1/2020 |
| JP | 2020171428 A | 10/2020 |
| KR | 20100103098 A | 9/2010 |
| KR | 101456942 B1 | 11/2014 |
| KR | 20150025830 A | 3/2015 |
| KR | 102047237 B1 | 12/2019 |
| RU | 2306921 C1 | 9/2007 |
| TW | I670047 B | 9/2019 |
| WO | 0187245 | 11/2001 |
| WO | 0191602 A2 | 12/2001 |
| WO | 02083737 A1 | 10/2002 |
| WO | 2011085727 A1 | 7/2011 |
| WO | 2017207455 A1 | 12/2017 |
| WO | 2018173073 A1 | 9/2018 |
| WO | 2018202065 A1 | 11/2018 |
| WO | 2019079895 A1 | 5/2019 |
| WO | 2019177451 A1 | 9/2019 |
| WO | 2021050928 A1 | 3/2021 |

OTHER PUBLICATIONS

"Jack Florek '17 presents at ACS in San Francisco", Emmanuel College, retrieved from http://gerdonlab.blogs.emmanuel.edu/2017/04/04/jack-florek-17-presents-acs-san-francisco/, Oct. 15, 2018, 6 pages.

All Office Actions, U.S. Appl. No. 17/326,505.

All Office Actions; U.S. Appl. No. 16/413,920.

All Office Actions; U.S. Appl. No. 16/441,749.

All Office Actions; U.S. Appl. No. 16/953,385.

Aram Huvis Co., Ltd, AramHuvis' skin & Hair Analysis System, APM (Aramo Professional Microscope), Jun. 15, 2017, pp. 1.

Artificial Intelligence in Skin and Hair Diagnostic Technology, year 2020, pp. 1.

Bawazer et al., " Efficient Selection of Biomineralizing DNA Aptamers Using Deep Sequencing and Population Clustering", ACS Nano, vol. 8, No. 1, 2014, pp. 1-10.

Benhabiles et al., "Deep learning based detection of hair loss levels from facial images", year 2019, pp. 6.

Chang et al., "A mobile device-based hairy scalp diagnosis system using deep learning techniques", IEEE 2nd Global Conference on Life Sciences and Technologies, year 2020, pp. 145-146.

Database WPI, XP002785798, Week 201649, 2017, Thomson Scientific, London GB, AN 2016-20069A, 1 pg.

Eifler, Electronic Nose-Based Fusarium Detection and Deoxynivalenol Aptamer Development, Dissertation, Jul. 2014, 106 pages.

Fujii et al., "Pesticide vapor sensing using an aptamer, nanopore, and agarose gel on a chip", Lab on a Chip, vol. 17, No. 14, 2017, pp. 2421-2425.

Gao et al., "Post-Selex optimization of aptamers", Analytical and Bioanalytical Chemistry, Springer, vol. 408, No. 17, 2016, pp. 4567-4573.

Geron, "Introducing Capsule Networks", O'Reilly, https://www.oreilly.com/content/introducing-capsule-networks/, Feb. 6, 2018, pp. 1-7.

H. Shih, "A precise automatic system for the hair assessment in hair-care diagnosis applications", Skin Research and Technology, 2015, pp. 500-507.

Hasegawa et al., "Methods for Improving Aptamer Binding Affinity", Molecules, vol. 21, No. 4, 2016, pp. 1-15.

Huang et al., "A cloud-based intelligent skin and scalp analysis system", Dec. 2018, 5 pages.

Hurot et al., "Bio-Inspired Strategies for Improving the Selectivityand Sensitivity of Artificial Noses: A Review". Sensors, vol. 20, No. 6, 2020, pp. 1-28.

Illuminate, powerpoint presentation, property of Aduivo Diagnostics PVT LTD, 10 pgs.

Infusing Technology to advance the growth of the Hair Care Industry, HairAnalysis—KritiKal, pp. 4.

Janas et al., "The selection of aptamers specific for membrane molecular targets", Cellular & Molecular Biology Letters, vol. 16, No. 1, 2011, pp. 25-39.

John et al., "ANYL 154: DNA aptamers that bind with high affinity to hydroxyapatite", ACS National Meeting & Exposition; 253rd National Meeting of The American-Chemical-Society (ACS) on Advanced Materials, Technologies, Systems, and Processes, American Chemical So, vol. 253, Apr. 2017, p. ANYL154.

Komarova et al., "Selection, Characterization, and Application of ss DNA Aptamer against Furaneol", Molecules, vol. 23, No. 12, 2018, pp. 1-15.

Kuznetsov et al., "Aptamer based vanillin sensor using an ion-sensitive field-effect transistor", Microchimica Acta, vol. 185, No. 1, 2017, 26 pages.

Lee et al., "An intelligent hair and scalp analysis system using camera sensors and Norwood-Hamilton model", International Journal of Innovative Computing, Information and Control, vol. 14, No. 2, pp. 503-518, Apr. 2018.

Li et al., "VEGF induces proliferation of human hair follicle dermal papilla cells through VEGFR-2-mediated activation of ERK", Experimental Cell Research, vol. 318, No. 14, 2012, pp. 1633-1640.

(56) References Cited

OTHER PUBLICATIONS

Low et al., "DNA aptamers bind specifically and selectively to (1-3)-beta-d-glucans", Biochemical and Biophysical Research Communications, vol. 378, No. 4, 2009, pp. 701-705.
Nonaka et al., "Screening and improvement of an anti-VEGF DNA aptamer", Molecules, vol. 15, No. 1, 2010, pp. 215-225.
Pillaiyar et al., "Downregulation of melanogenesis: drug discovery and therapeutic options", Drug Discovery Today, vol. 22, No. 2, Feb. 2017, pp. 282-298.
Ramos et al., "Female Pattern Hair Loss: A Clinical and Pathophysiological Review", ABD: Anais Brasileiros De Dermatologia, vol. 90, No. 4, Jul.-Aug. 2015, pp. 1-29.
Schwartz et al., "The role of oxidative damage in poor scalp health: ramifications to causality and associated hair growth", International Journal of Cosmetic Science, vol. 37, No. Suppl. 2, 2015, pp. 9-15.
Shibata et al., "The cell wall galactomannan antigen from Malassezia furfur and Malassezia pachydermatis contains -1,6-linked linear galactofuranosyl residues and its detection has diagnostic potential", Microbiology, vol. 155, No. 10, 2009, pp. 3420-3429.
Su et al., "An Intelligent Scalp Inspection and Diagnosis System for Caring Hairy Scalp Health", pp. 508-509, 2018.
Tang et al., "Improved detection of deeply invasive candidiasis with DNA aptamers specific binding to (1-3)-[beta]-D-glucans from Candida albicans", European Journal of Clinical Microbiology & Infectious diseases, vol. 35, No. 4, 2016, pp. 587-595.
Unpublished U.S. Appl. No. 16/953,385, filed Nov. 20, 2020, to Supriya Punyani et al.
Unpublished U.S. Appl. No. 17/326,505, filed May 21, 2021, to first inventor Supriya Punyani et al.
Velegraki et al., "Malassezia Infections in Humans and Animals: Pathophysiology, Detection and Treatment", PLOS Pathogens, vol. 11, No. 1, Jan. 2015, pp. 1-6.
Wan-Jung Chang et al., "ScalpEye: A Deep Learning Based Scalp Hair Inspection and Diagnosis System for Scalp Health", IEEE Access, Jul. 21, 2020, vol. 8, Digital Object Identifier 10.1109/Access.2020.3010847, pp. 134826-134837.
Wang et al., "Development and experimental evaluation of machine-learning techniques for an intelligent hairy scalp detection system", Applied Sciences, pp. 28, 2018.
"Connected scalp advisor shows root of the problem" URL Link: https://www.youtube.com/watch?v=Y-oAEiCO1-g, Jan. 9, 2019.
16019 PCT Search Report and Written Opinion for PCT/US2022/024553 dated Jul. 25, 2022, 15 pages.
Chai et al. "Auto Hair: Fully Automatic Hair Modeling from A Single Image", ACM Transactions on Graphics, vol. 35, Issue 4, Jul. 11, 2016, Article No. 116, pp. 1-12.
Chen et al. "A portable wireless scalp inspector and its automatic diagnosis system based on deep learning techniques", The 16th International Symposium on Advanced Technology, Nov. 1- Nov. 2, 2017, Hachioji, Kogakuin Univ., p. 220.
Harries et al. "Towards a consensus on how to diagnose and quantify female pattern hair loss—The 'Female Pattern Hair Loss Severity Index'", Journal of the European Academy of Dermatology and Venereology, Year 2016, vol. 30, Issue 4, pp. 667-676.
Ludwig et al. "Classification of the types of androgenetic alopecia(common baldness) occurring in the female sex", British Journal of Dermatology dated Mar. 21, 1977, 97, pp. 247-254.
Sabour et al. "Dynamic Routing Between Capsules", 31st Conference on Neural Information Processing Systems (NIPS 2017), Long Beach, CA, USA, pp. 1-11.
The Japanese Journal of Dermatology, 127 (13), year 2017, pp. 2763-2777.
Wisuwath Sunhem et al. "An approach to face shape classification fo hairstyle recommendation", 8th International Conference on Advanced Computational Intelligence, Chiang Mai, Thailand; Feb. 14-16, 2016, pp. 390-394.
Chao Sun et al. "Hairstyle Pattern Recognition based on CNNs", IEEE International Conference on Systems, Man, and Cybernetics (SMC), Oct. 5-8, 2017, pp. 1840-1845.
Shinobu Nagase et al. "Changes in structure and geometric properties of human hair by aging", Journal of Cosmetic Science, vol. 60, Nov./Dec. 2009, pp. 637-648.
Wisuwat Sunhem et al., "An Approach to Face Shape Classification for Hairstyle Recommendation", 8th International Conference on Advanced Computational Intelligence, Feb. 14-16, 2016, pp. 390-394.
All Office Actions; U.S. Appl. No. 16/587,224.
All Office Actions; U.S. Appl. No. 17/386,580.
Unpublished U.S. Appl. No. 17/386,580, filed Jul. 28, 2021, to Ankur Purwar et al.
Xi, et al., "Capsule Network Performance on Complex Data", arxiv.org, Cornell University Library, 201 Olin Library Cornell University Ithaca, NY 14853, Dec. 10, 2017, 7 Pages.

* cited by examiner

DIGITAL IMAGING AND LEARNING SYSTEMS AND METHODS FOR ANALYZING PIXEL DATA OF A SCALP REGION OF A USERS SCALP TO GENERATE ONE OR MORE USER-SPECIFIC SCALP CLASSIFICATIONS

FIELD

The present disclosure generally relates to digital imaging and learning systems and methods, and more particularly to, digital imaging and learning systems and methods for analyzing pixel data of a scalp region of a user's scalp to generate one or more user-specific scalp classifications.

BACKGROUND

Generally, multiple endogenous factors of human hair and skin, such as sebum and sweat, have a real-world impact on the overall health of a user's scalp, which may include scalp skin health (e.g., white sebum residue, scalp skin cracks/lines) and follicle/hair health (e.g., acne, scalp plugs). Additional exogenous factors, such as wind, humidity, and/or usage of various hair-related products, may also affect the health of a user's scalp. Moreover, the user's perception of scalp related issues typically does not reflect such underlying endogenous and/or exogenous factors.

Thus a problem arises given the number of endogenous and/or exogenous factors in conjunction with the complexity of scalp and hair types, especially when considered across different users, each of whom may be associated with different demographics, races, and ethnicities. This creates a problem in the diagnosis and treatment of various human scalp conditions and characteristics. For example, prior art methods, including personal consumer product trials can be time consuming or error prone (and possibly negative). In addition, a user may attempt to empirically experiment with various products or techniques, but without achieving satisfactory results and/or causing possible negative side effects, impacting the health or otherwise visual appearance of his or her scalp.

For the foregoing reasons, there is a need for digital imaging and learning systems and methods for analyzing pixel data of a scalp region of a user's scalp to generate one or more user-specific scalp classifications.

SUMMARY

Generally, as described herein, digital imaging and learning systems are described for analyzing pixel data of a scalp region of a user's scalp to generate one or more user-specific scalp classifications. Such digital imaging and learning systems provide a digital imaging, and artificial intelligence (AI), based solution for overcoming problems that arise from the difficulties in identifying and treating various endogenous and/or exogenous factors or attributes affecting the health of a human scalp.

The digital imaging and learning systems as described herein allow a user to submit a specific user image to imaging server(s) (e.g., including its one or more processors), or otherwise a computing device (e.g., such as locally on the user's mobile device), where the imaging server(s) or user computing device, implements or executes an artificial intelligence based scalp based learning model trained with pixel data of potentially 10,000s (or more) images depicting scalp regions of scalps of respective individuals. The scalp based learning model may generate, based on an image classification of the user's scalp region, at least one user-specific scalp classification designed to address at least one feature identifiable within the pixel data comprising the at least the portion of a scalp region of the user's scalp. For example, at least one portion of a scalp region of the user's scalp can comprise pixels or pixel data indicative of white sebum, irritation, acne, scalp plugs, and/or other attributes/conditions of a specific user's scalp skin or hair follicle regions. In some embodiments, the user-specific scalp classification (and/or product specific scalp classification) may be transmitted via a computer network to a user computing device of the user for rendering on a display screen. In other embodiments, no transmission to the imaging server of the user's specific image occurs, where the user-specific scalp classification (and/or product specific scalp classification) may instead be generated by the scalp based learning model, executing and/or implemented locally on the user's mobile device and rendered, by a processor of the mobile device, on a display screen of the mobile device. In various embodiments, such rendering may include graphical representations, overlays, annotations, and the like for addressing the feature in the pixel data.

More specifically, as described herein, a digital imaging and learning system is disclosed. The digital imaging and learning system is configured to analyze pixel data of an image of a scalp region of a user's scalp to generate one or more user-specific scalp classifications. The digital imaging and learning system may include one or more processors and an imaging application (app) comprising computing instructions configured to execute on the one or more processors. The digital imaging and learning system may further comprise a scalp based learning model, accessible by the imaging app, and trained with pixel data of a plurality of training images depicting scalp regions of scalps of respective individuals. The scalp based learning model may be configured to output one or more image classifications corresponding to one or more features of scalp skin or hair follicle regions of the respective individuals. Still further, in various embodiments, computing instructions of the imaging app, when executed by the one or more processors, may cause the one or more processors to receive an image of a user. The image may comprise a digital image as captured by an imaging device. The image may comprise pixel data of at least a portion of a scalp region of the user's scalp. The computing instructions of the imaging app, when executed by the one or more processors, may further cause the one or more processors to analyze, by the scalp based learning model, the image as captured by the imaging device to determine at least one image classification of the user's scalp region. The at least one image classification may be selected from the one or more image classifications of the scalp based learning model. The computing instructions of the imaging app, when executed by the one or more processors, may further cause the one or more processors to generate, based on the at least one image classification of the user's scalp region, a user-specific scalp classification designed to address at least one feature identifiable within the pixel data comprising the at least the portion of a scalp region of the user's scalp.

In addition, as described herein, a digital imaging and learning method is disclosed for analyzing pixel data of an image of a scalp region of a user's scalp to generate one or more user-specific scalp classifications. The digital imaging and learning method comprises receiving, at an imaging application (app) executing on one or more processors, an image of a user. The image may be a digital image as captured by an imaging device. In addition, the image may comprise pixel data of at least a portion of a scalp region of the user's scalp. The digital imaging and learning method further may further comprise analyzing, by a scalp based learning model accessible by the imaging app, the image as captured by the imaging device to determine at least one image classification of the user's scalp region. The at least one image classification may be selected from one or more image classifications of the scalp based learning model. In addition, the scalp based learning model may be trained with pixel data of a plurality of training images depicting scalp regions of scalps of respective individuals. Still further, the scalp based learning model may be operable to output the one or more image classifications corresponding to one or more features of scalp skin or hair follicle regions of the respective individuals. The digital imaging and learning method further comprises generating, by the imaging app based on the at least one image classification of the user's scalp region, a user-specific scalp classification designed to address at least one feature identifiable within the pixel data comprising the at least the portion of a scalp region of the user's scalp.

Further, as described herein, a tangible, non-transitory computer-readable medium storing instructions for analyzing pixel data of an image of a scalp region of a user's scalp to generate one or more user-specific scalp classifications is disclosed. The instructions, when executed by one or more processors, may cause the one or more processors to receive, at an imaging application (app), an image of a user. The image may comprise a digital image as captured by an imaging device. The image may comprise pixel data of at least a portion of a scalp region of the user's scalp. The instructions, when executed by one or more processors, may further cause the one or more processors to analyze, by a scalp based learning model accessible by the imaging app, the image as captured by the imaging device to determine at least one image classification of the user's scalp region. The at least one image classification may be selected from one or more image classifications of the scalp based learning model. The scalp based learning model may be trained with pixel data of a plurality of training images depicting scalp regions of scalps of respective individuals. In addition, the scalp based learning model may be operable to output one or more image classifications corresponding to one or more features of scalp skin or hair follicle regions of the respective individuals. The instructions, when executed by one or more processors, may further cause the one or more processors to generate, by the imaging app based on the at least one image classification of the user's scalp region, a user-specific scalp classification designed to address at least one feature identifiable within the pixel data comprising the at least the portion of a scalp region of the user's scalp.

In accordance with the above, and with the disclosure herein, the present disclosure includes improvements in computer functionality or in improvements to other technologies at least because the disclosure describes that, e.g., an imaging server, or otherwise computing device (e.g., a user computer device), is improved where the intelligence or predictive ability of the imaging server or computing device is enhanced by a trained (e.g., machine learning trained) scalp based learning model. The scalp based learning model, executing on the imaging server or computing device, is able to more accurately identify, based on pixel data of other individuals, one or more of a user-specific scalp skin or hair follicle region feature, an image classification of the user's scalp region, and/or a user-specific scalp classification designed to address at least one feature identifiable within the pixel data comprising the at least the portion of a scalp region of the user's scalp. That is, the present disclosure describes improvements in the functioning of the computer itself or "any other technology or technical field" because an imaging server or user computing device is enhanced with a plurality of training images (e.g., 10,000s of training images and related pixel data as feature data) to accurately predict, detect, or determine pixel data of a user-specific images, such as newly provided customer images. This improves over the prior art at least because existing systems lack such predictive or classification functionality and are simply not capable of accurately analyzing user-specific images to output a predictive result to address at least one feature identifiable within the pixel data comprising the at least the portion of a scalp region of the user's scalp.

For similar reasons, the present disclosure relates to improvements to other technologies or technical fields at least because the present disclosure describes or introduces improvements to computing devices in the scalp skin/hair follicle care field and scalp care/hair follicle products field, whereby the trained scalp based learning model executing on the imaging device(s) or computing devices improves the field of scalp skin and hair follicle region care, and chemical formulations and scalp classifications thereof, with digital and/or artificial intelligence based analysis of user or individual images to output a predictive result to address user-specific pixel data of at least one feature identifiable within the pixel data comprising the at least the portion of a scalp region of the user's scalp.

In addition, the present disclosure relates to improvement to other technologies or technical fields at least because the present disclosure describes or introduces improvements to computing devices in the scalp skin/hair follicle care field and scalp care/hair follicle products field, whereby the trained scalp based learning model executing on the imaging device(s) or computing devices improve the underlying computer device (e.g., imaging server(s) and/or user computing device), where such computer devices are made more efficient by the configuration, adjustment, or adaptation of a given machine-learning network architecture. For example, in some embodiments, fewer machine resources (e.g., processing cycles or memory storage) may be used by decreasing computational resources by decreasing machine-learning network architecture needed to analyze images, including by reducing depth, width, image size, or other machine-learning based dimensionality requirements. Such reduction frees up the computational resources of an underlying computing system, thereby making it more efficient.

Still further, the present disclosure relates to improvement to other technologies or technical fields at least because the present disclosure describes or introduces improvements to computing devices in the field of security, where images of users are preprocessed (e.g., cropped or otherwise modified) to define extracted or depicted scalp regions of a user without depicting personal identifiable information (PII) of the user. For example, simple cropped or redacted portions of an image of a user may be used by the scalp based learning model described herein, which eliminates the need of transmission of private photographs of users across a computer network (where such images may be susceptible of interception by third parties). Such features provide a security improvement, i.e., where the removal of PII (e.g., facial features) provides an improvement over prior systems because cropped or redacted images, especially ones that may be transmitted over a network (e.g., the Internet), are more secure without including PII information of a user. Accordingly, the systems and methods described herein operate without the need for such non-essential information, which provides an improvement, e.g., a security improvement, over prior system. In addition, the use of cropped images, at least in some embodiments, allows the underlying system to store and/or process smaller data size images, which results in a performance increase to the underlying system as a whole because the smaller data size images require less storage memory and/or processing resources to store, process, and/or otherwise manipulate by the underlying computer system.

In addition, the present disclosure includes applying certain of the claim elements with, or by use of, a particular machine, e.g., an imaging device, which captures images used to train the scalp based learning model and used to determine an image classification corresponding to one or more features of the user's scalp region.

In addition, the present disclosure includes specific features other than what is well-understood, routine, conventional activity in the field, or adding unconventional steps that confine the claim to a particular useful application, e.g., analyzing pixel data of an image of a scalp region of a user's scalp to generate one or more user-specific scalp classifications.

Advantages will become more apparent to those of ordinary skill in the art from the following description of the preferred embodiments which have been shown and described by way of illustration. As will be realized, the present embodiments may be capable of other and different embodiments, and their details are capable of modification in various respects. Accordingly, the drawings and description are to be regarded as illustrative in nature and not as restrictive.

BRIEF DESCRIPTION OF THE DRAWINGS

The Figures described below depict various aspects of the system and methods disclosed therein. It should be understood that each Figure depicts an embodiment of a particular aspect of the disclosed system and methods, and that each of the Figures is intended to accord with a possible embodiment thereof. Further, wherever possible, the following description refers to the reference numerals included in the following Figures, in which features depicted in multiple Figures are designated with consistent reference numerals.

There are shown in the drawings arrangements which are presently discussed, it being understood, however, that the present embodiments are not limited to the precise arrangements and instrumentalities shown, wherein.

The Figures depict preferred embodiments for purposes of illustration only. Alternative embodiments of the systems and methods illustrated herein may be employed without departing from the principles of the invention described herein.

DETAILED DESCRIPTION OF THE INVENTION

Figure 1:
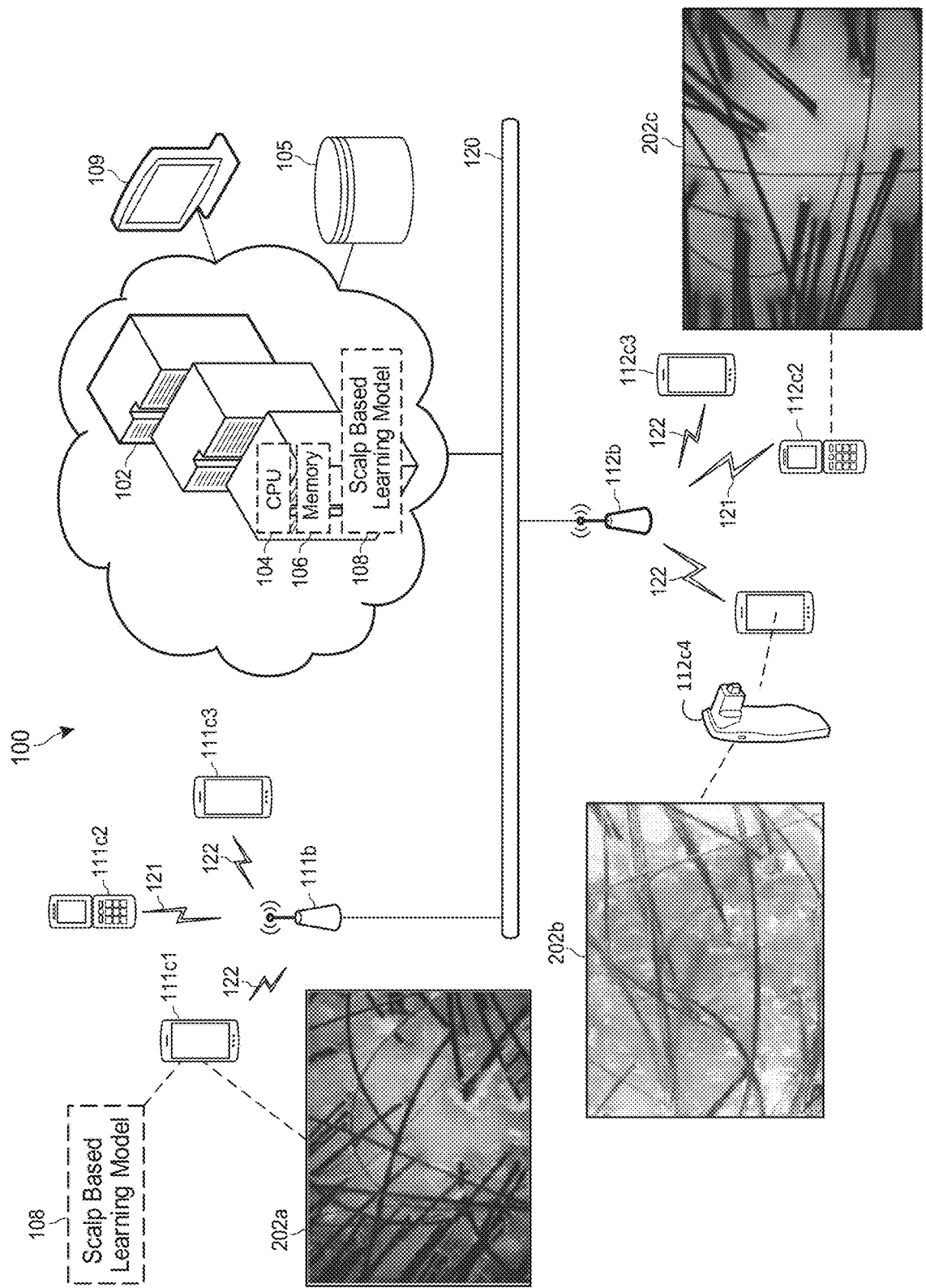
FIG. 1 illustrates an example digital imaging and learning system configured to analyze pixel data of an image of a scalp region of a user's scalp to generate one or more user-specific scalp classifications, in accordance with various embodiments disclosed herein.

FIG. 1 illustrates an example digital imaging and learning system 100 configured to analyze pixel data of an image (e.g., any one or more of images 202*a*, 202*b*, and/or 202*c*) of a scalp region of a user's scalp to generate one or more user-specific scalp classifications, in accordance with various embodiments disclosed herein. Generally, as referred to herein, a scalp region of the user's scalp may refer to one or more of a front scalp region, a back scalp region, a side scalp region, a top scalp region, a full scalp region, a partial scalp region, or a custom defined scalp region (e.g., a custom perspective region) of a scalp of a given user. In the example embodiment of FIG. 1, digital imaging and learning system 100 includes server(s) 102, which may comprise one or more computer servers. In various embodiments server(s) 102 comprise multiple servers, which may comprise multiple, redundant, or replicated servers as part of a server farm. In still further embodiments, server(s) 102 may be implemented as cloud-based servers, such as a cloud-based computing platform. For example, imaging server(s) 102 may be any one or more cloud-based platform(s) such as MICROSOFT AZURE, AMAZON AWS, or the like. Server(s) 102 may include one or more processor(s) 104 as well as one or more computer memories 106. In various embodiments, server(s) 102 may be referred to herein as "imaging server(s)."

Memories 106 may include one or more forms of volatile and/or non-volatile, fixed and/or removable memory, such as read-only memory (ROM), electronic programmable read-only memory (EPROM), random access memory (RAM), erasable electronic programmable read-only memory (EEPROM), and/or other hard drives, flash memory, MicroSD cards, and others. Memorie(s) 106 may store an operating system (OS) (e.g., Microsoft Windows, Linux, UNIX, etc.) capable of facilitating the functionalities, apps, methods, or other software as discussed herein. Memorie(s) 106 may also store a scalp based learning model 108, which may be an artificial intelligence based model, such as a machine learning model, trained on various images (e.g., images 202*a*, 202*b*, and/or 202*c*), as described herein. Additionally, or alternatively, the scalp based learning model 108 may also be stored in database 105, which is accessible or otherwise communicatively coupled to imaging server(s) 102. In addition, memories 106 may also store machine readable instructions, including any of one or more application(s) (e.g., an imaging application as described herein), one or more software component(s), and/or one or more application programming interfaces (APIs), which may be implemented to facilitate or perform the features, functions, or other disclosure described herein, such as any methods, processes, elements or limitations, as illustrated, depicted, or described for the various flowcharts, illustrations, diagrams, figures, and/or other disclosure herein. For example, at least some of the applications, software components, or APIs may be, include, otherwise be part of, an imaging based machine learning model or component, such as the scalp based learning model 108, where each may be configured to facilitate their various functionalities discussed herein. It should be appreciated that one or more other applications may be envisioned and that are executed by the processor(s) 104.

The processor(s) 104 may be connected to the memories 106 via a computer bus responsible for transmitting electronic data, data packets, or otherwise electronic signals to and from the processor(s) 104 and memories 106 in order to implement or perform the machine readable instructions, methods, processes, elements or limitations, as illustrated, depicted, or described for the various flowcharts, illustrations, diagrams, figures, and/or other disclosure herein.

Processor(s) 104 may interface with memory 106 via the computer bus to execute an operating system (OS). Processor(s) 104 may also interface with the memory 106 via the computer bus to create, read, update, delete, or otherwise access or interact with the data stored in memories 106 and/or the database 104 (e.g., a relational database, such as Oracle, DB2, MySQL, or a NoSQL based database, such as MongoDB). The data stored in memories 106 and/or database 105 may include all or part of any of the data or information described herein, including, for example, training images and/or user images (e.g., including any one or more of images 202*a*, 202*b*, and/or 202*c*; scalp images (e.g., 302*l*, 302*m*, 302*h*, 312*l*, 312*m*, 312*h*, 322*l*, 322*m*, and 322*h*); and/or other images and/or information of the user, including demographic, age, race, skin type, hair type, hair style, or the like, or as otherwise described herein.

Imaging server(s) 102 may further include a communication component configured to communicate (e.g., send and receive) data via one or more external/network port(s) to one or more networks or local terminals, such as computer network 120 and/or terminal 109 (for rendering or visualizing) described herein. In some embodiments, imaging server(s) 102 may include a client-server platform technology such as ASP.NET, Java J2EE, Ruby on Rails, Node.js, a web service or online API, responsive for receiving and responding to electronic requests. The imaging server(s) 102 may implement the client-server platform technology that may interact, via the computer bus, with the memories(s) 106 (including the applications(s), component(s), API(s), data, etc. stored therein) and/or database 105 to implement or perform the machine readable instructions, methods, processes, elements or limitations, as illustrated, depicted, or described for the various flowcharts, illustrations, diagrams, figures, and/or other disclosure herein.

In various embodiments, the imaging server(s) 102 may include, or interact with, one or more transceivers (e.g., WWAN, WLAN, and/or WPAN transceivers) functioning in accordance with IEEE standards, 3GPP standards, or other standards, and that may be used in receipt and transmission of data via external/network ports connected to computer network 120. In some embodiments, computer network 120 may comprise a private network or local area network (LAN). Additionally, or alternatively, computer network 120 may comprise a public network such as the Internet.

Imaging server(s) 102 may further include or implement an operator interface configured to present information to an administrator or operator and/or receive inputs from the administrator or operator. As shown in FIG. 1, an operator interface may provide a display screen (e.g., via terminal 109). Imaging server(s) 102 may also provide I/O components (e.g., ports, capacitive or resistive touch sensitive input panels, keys, buttons, lights, LEDs), which may be directly accessible via, or attached to, imaging server(s) 102 or may be indirectly accessible via or attached to terminal 109. According to some embodiments, an administrator or operator may access the server 102 via terminal 109 to review information, make changes, input training data or images, initiate training of hair based learning model 108, and/or perform other functions.

As described herein, in some embodiments, imaging server(s) 102 may perform the functionalities as discussed herein as part of a "cloud" network or may otherwise communicate with other hardware or software components within the cloud to send, retrieve, or otherwise analyze data or information described herein.

In general, a computer program or computer based product, application, or code (e.g., the model(s), such as AI models, or other computing instructions described herein) may be stored on a computer usable storage medium, or tangible, non-transitory computer-readable medium (e.g., standard random access memory (RAM), an optical disc, a universal serial bus (USB) drive, or the like) having such computer-readable program code or computer instructions embodied therein, wherein the computer-readable program code or computer instructions may be installed on or otherwise adapted to be executed by the processor(s) 104 (e.g., working in connection with the respective operating system in memories 106) to facilitate, implement, or perform the machine readable instructions, methods, processes, elements or limitations, as illustrated, depicted, or described for the various flowcharts, illustrations, diagrams, figures, and/or other disclosure herein. In this regard, the program code may be implemented in any desired program language, and may be implemented as machine code, assembly code, byte code, interpretable source code or the like (e.g., via Golang, Python, C, C++, C#, Objective-C, Java, Scala, ActionScript, JavaScript, HTML, CSS, XML, etc.).

As shown in FIG. 1, imaging server(s) 102 are communicatively connected, via computer network 120 to the one or more user computing devices 111*c*1-111*c*3 and/or 112*c*1-112*c*4 via base stations 111*b* and 112*b*. In some embodiments, base stations 111*b* and 112*b* may comprise cellular base stations, such as cell towers, communicating to the one or more user computing devices 111*c*1-111*c*3 and 112*c*1-112*c*4 via wireless communications 121 based on any one or more of various mobile phone standards, including NMT, GSM, CDMA, UMMTS, LTE, 5G, or the like.

Additionally, or alternatively, base stations 111*b* and 112*b* may comprise routers, wireless switches, or other such wireless connection points communicating to the one or more user computing devices 111*c*1-111*c*3 and 112*c*1-112*c*4 via wireless communications 122 based on any one or more of various wireless standards, including by non-limiting example, IEEE 802.11a/b/c/g (WIFI), the BLUETOOTH standard, or the like.

Any of the one or more user computing devices 111*c*1-111*c*3 and/or 112*c*1-112*c*4 may comprise mobile devices and/or client devices for accessing and/or communications with imaging server(s) 102. Such mobile devices may comprise one or more mobile processor(s) and/or an imaging device for capturing images, such as images as described herein (e.g., any one or more of images 202*a*, 202*b*, and/or 202*c*). In various embodiments, user computing devices 111*c*1-111*c*3 and/or 112*c*1-112*c*3 may comprise a mobile phone (e.g., a cellular phone), a tablet device, a personal data assistance (PDA), or the like, including, by non-limiting example, an APPLE iPhone or iPad device or a GOOGLE ANDROID based mobile phone or table.

In additional embodiments, the user computing device 112*c*4 may be a portable microscope device that a user may use to capture detailed images of the user's scalp. Specifically, the portable microscope device 112*c*4 may include a microscopic camera that is configured to capture images (e.g., any one or more of images 202a, 202b, and/or 202c) at an approximately microscopic level of a scalp region of a user's scalp. For example, unlike any of the user computing devices 111c1-111c3 and 112c1-112c3, the portable microscope device 112c4 may capture detailed, high-magnification (e.g., 2 megapixels for 60-200 times magnification) images of the user's scalp while maintaining physical contact with the user's scalp. As a particular example, the portable microscope device 112c4 may be the API 202 HAIR SCALP ANALYSIS DEVICE, developed by ARAM HUVIS. In certain embodiments, the portable microscope device 112c4 may also include a display or user interface configured to display the captured images and/or the results of the image analysis to the user.

Additionally, or alternatively, the portable microscope device 112c4 may be communicatively coupled to a user computing device 112c1 (e.g., a user's mobile phone) via a WiFi connection, a BLUETOOTH connection, and/or any other suitable wireless connection, and the portable microscope device 112c4 may be compatible with a variety of operating platforms (e.g., Windows, iOS, Android, etc.). Thus, the portable microscope device 112c4 may transmit the captured images to the user computing device 112c1 for analysis and/or display to the user. Moreover, the portable microscope device 112c4 may be configured to capture high-quality video of a user's scalp, and may stream the high-quality video of the user's scalp to a display of the portable microscope device 112c4 and/or a communicatively coupled user computing device 112c1 (e.g., a user's mobile phone). In certain additional embodiments, the components of each of the portable microscope device 112c4 and the communicatively connected user computing device 112c1 may be incorporated into a singular device.

In additional embodiments, user computing devices 111c1-111c3 and/or 112c1-112c3 may comprise a retail computing device. A retail computing device may comprise a user computer device configured in a same or similar manner as a mobile device, e.g., as described herein for user computing devices 111c1-111c3, including having a processor and memory, for implementing, or communicating with (e.g., via server(s) 102), a scalp based learning model 108 as described herein. Additionally, or alternatively, a retail computing device may be located, installed, or otherwise positioned within a retail environment to allow users and/or customers of the retail environment to utilize the digital imaging and learning systems and methods on site within the retail environment. For example, the retail computing device may be installed within a kiosk for access by a user. The user may then upload or transfer images (e.g., from a user mobile device) to the kiosk to implement the digital imaging and learning systems and methods described herein. Additionally, or alternatively, the kiosk may be configured with a camera to allow the user to take new images (e.g., in a private manner where warranted) of himself or herself for upload and transfer. In such embodiments, the user or consumer himself or herself would be able to use the retail computing device to receive and/or have rendered a user-specific electronic scalp classification, as described herein, on a display screen of the retail computing device.

Additionally, or alternatively, the retail computing device may be a mobile device (as described herein) as carried by an employee or other personnel of the retail environment for interacting with users or consumers on site. In such embodiments, a user or consumer may be able to interact with an employee or otherwise personnel of the retail environment, via the retail computing device (e.g., by transferring images from a mobile device of the user to the retail computing device or by capturing new images by a camera of the retail computing device), to receive and/or have rendered a user-specific electronic scalp classification, as described herein, on a display screen of the retail computing device.

In various embodiments, the one or more user computing devices 111c1-111c3 and/or 112c1-112c4 may implement or execute an operating system (OS) or mobile platform such as Apple's iOS and/or Google's Android operation system. Any of the one or more user computing devices 111c1-111c3 and/or 112c1-112c4 may comprise one or more processors and/or one or more memories for storing, implementing, or executing computing instructions or code, e.g., a mobile application or a home or personal assistant application, as described in various embodiments herein. As shown in FIG. 1, scalp based learning model 108 and/or an imaging application as described herein, or at least portions thereof, may also be stored locally on a memory of a user computing device (e.g., user computing device 111c1).

User computing devices 111c1-111c3 and/or 112c1-112c4 may comprise a wireless transceiver to receive and transmit wireless communications 121 and/or 122 to and from base stations 111b and/or 112b. In various embodiments, pixel based images (e.g., images 202a, 202b, and/or 202c) may be transmitted via computer network 120 to imaging server(s) 102 for training of model(s) (e.g., scalp based learning model 108) and/or imaging analysis as described herein.

In addition, the one or more user computing devices 111c1-111c3 and/or 112c1-112c4 may include an imaging device and/or digital video camera for capturing or taking digital images and/or frames (e.g., which can be any one or more of images 202a, 202b, and/or 202c). Each digital image may comprise pixel data for training or implementing model(s), such as AI or machine learning models, as described herein. For example, an imaging device and/or digital video camera of, e.g., any of user computing devices 111c1-111c3 and/or 112c1-112c4, may be configured to take, capture, or otherwise generate digital images (e.g., pixel based images 202a, 202b, and/or 202c) and, at least in some embodiments, may store such images in a memory of a respective user computing devices. Additionally, or alternatively, such digital images may also be transmitted to and/or stored on memorie(s) 106 and/or database 105 of server(s) 102.

Still further, each of the one or more user computer devices 111c1-111c3 and/or 112c1-112c4 may include a display screen for displaying graphics, images, text, product scalp classifications, data, pixels, features, and/or other such visualizations or information as described herein. In various embodiments, graphics, images, text, product scalp classifications, data, pixels, features, and/or other such visualizations or information may be received from imaging server(s) 102 for display on the display screen of any one or more of user computer devices 111c1-111c3 and/or 112c1-112c4. Additionally, or alternatively, a user computer device may comprise, implement, have access to, render, or otherwise expose, at least in part, an interface or a guided user interface (GUI) for displaying text and/or images on its display screen.

In some embodiments, computing instructions and/or applications executing at the server (e.g., server(s) 102) and/or at a mobile device (e.g., mobile device 111c1) may be communicatively connected for analyzing pixel data of an image of a scalp region of a user's scalp to generate one or more user-specific scalp classifications, as described herein. For example, one or more processors (e.g., processor(s) 104) of server(s) 102 may be communicatively coupled to a mobile device via a computer network (e.g., computer network 120). In such embodiments, an imaging app may comprise a server app portion configured to execute on the one or more processors of the server (e.g., server(s) 102) and a mobile app portion configured to execute on one or more processors of the mobile device (e.g., any of one or more user computing devices 111c1-111c3 and/or 112c1-112c3) and/or standalone imaging device (e.g., user computing device 112c4). In such embodiments, the server app portion is configured to communicate with the mobile app portion. The server app portion or the mobile app portion may each be configured to implement, or partially implement, one or more of: (1) receiving the image captured by the imaging device; (2) determining the image classification of the user's scalp; (3) generating the user-specific scalp classification; and/or (4) transmitting the one user-specific scalp classification to the mobile app portion.

Figure 2:
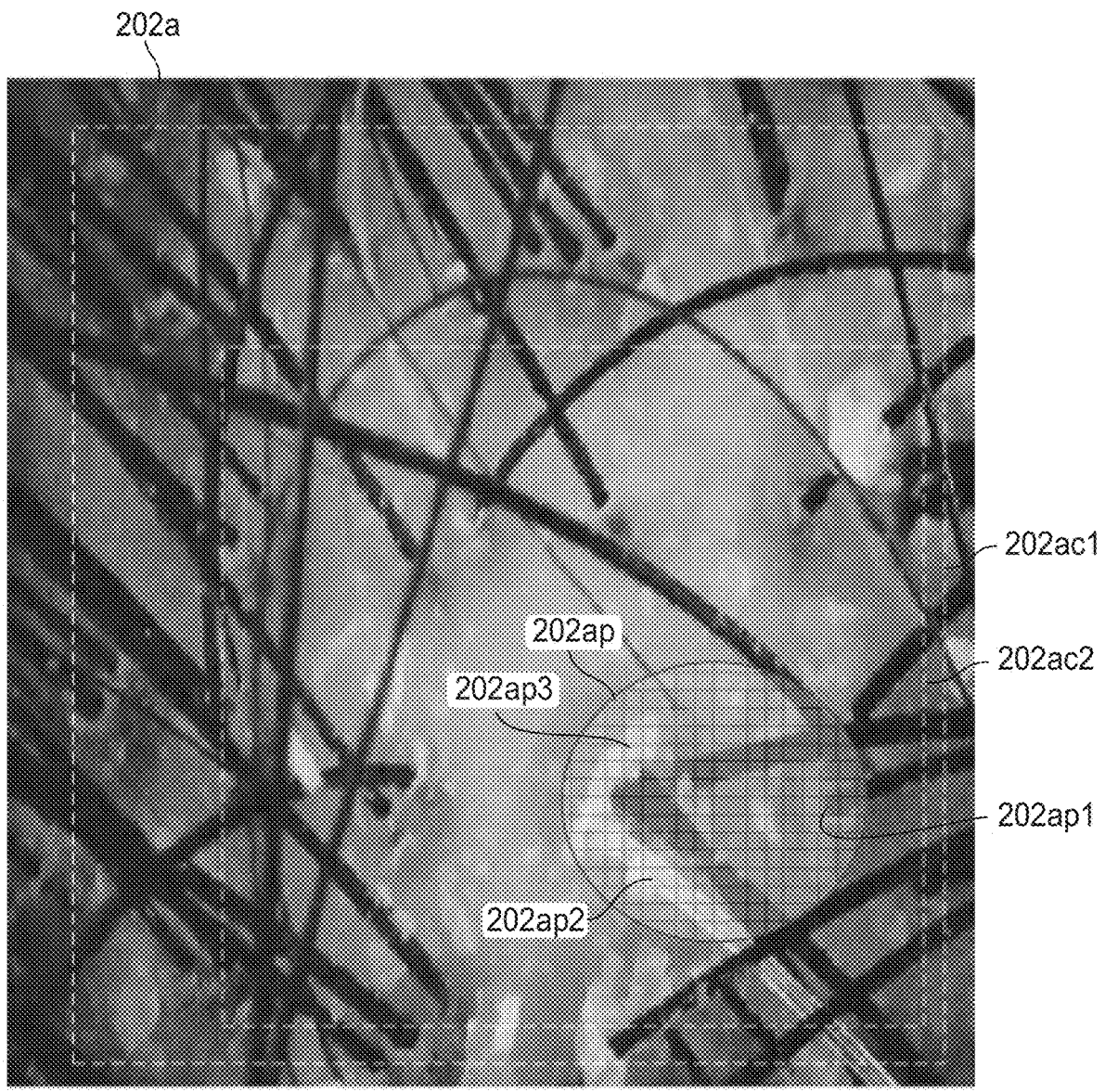
FIG. 2 illustrates an example image and its related pixel data that may be used for training and/or implementing a scalp based learning model, in accordance with various embodiments disclosed herein.

FIG. 2 illustrates an example image 202a and its related pixel data that may be used for training and/or implementing a scalp based learning model, in accordance with various embodiments disclosed herein. In various embodiments, as shown for FIG. 1, image 202a may be an image captured by a user (e.g., user 202au). Image 202a (as well as images 202b and/or 202c of user 202bu and user 202cu, respectively) may be transmitted to server(s) 102 via computer network 120, as shown for FIG. 1. It is to be understood that such images may be captured by the users themselves or, additionally or alternatively, others, such as a retailer, etc., where such images are used and/or transmitted on behalf of a user.

More generally, digital images, such as example images 202a, 202b, and 202c, may be collected or aggregated at imaging server(s) 102 and may be analyzed by, and/or used to train, a scalp based learning model (e.g., an AI model such as a machine learning imaging model as described herein). Each of these images may comprise pixel data (e.g., RGB data) comprising feature data and corresponding to scalp regions of respective users, within the respective image. The pixel data may be captured by an imaging device of one of the user computing devices (e.g., one or more user computer devices 111c1-111c3 and/or 112c1-112c4).

With respect to digital images as described herein, pixel data (e.g., pixel data 202ap of FIG. 2) comprises individual points or squares of data within an image, where each point or square represents a single pixel (e.g., each of pixel 202ap1, pixel 202ap2, and pixel 202ap3) within an image. Each pixel may be at a specific location within an image. In addition, each pixel may have a specific color (or lack thereof). Pixel color, may be determined by a color format and related channel data associated with a given pixel. For example, a popular color format is a 1976 CIELAB (also referenced herein as the "CIE L*-a*-b*" or simply "L*a*b*" color format) color format that is configured to mimic the human perception of color. Namely, the L*a*b* color format is designed such that the amount of numerical change in the three values representing the L*a*b* color format (e.g., L*, a*, and b*) corresponds roughly to the same amount of visually perceived change by a human. This color format is advantageous, for example, because the L*a*b* gamut (e.g., the complete subset of colors included as part of the color format) includes both the gamuts of Red (R), Green (G), and Blue (B) (collectively RGB) and Cyan (C), Magenta (M), Yellow (Y), and Black (K) (collectively CMYK) color formats.

In the L* a* b* color format, color is viewed as point in three dimensional space, as defined by the three-dimensional coordinate system (L*, a*, b*), where each of the L* data, the a* data, and the b* data may correspond to individual color channels, and may therefore be referenced as channel data. In this three-dimensional coordinate system, the L* axis describes the brightness (luminance) of the color with values from 0 (black) to 100 (white). The a* axis describes the green or red ratio of a color with positive a* values (+a*) indicating red hue and negative a* values (−a*) indicating green hue. The b* axis describes the blue or yellow ratio of a color with positive b* values (+b*) indicating yellow hue and negative b* values (−b*) indicating blue hue. Generally, the values corresponding to the a* and b* axes may be unbounded, such that the a* and b* axes may include any suitable numerical values to express the axis boundaries. However, the a* and b* axes may typically include lower and upper boundaries that range from approximately 150 to −150. Thus, in this manner, each pixel color value may be represented as a three-tuple of the L*, a*, and b* values to create a final color for a given pixel.

As another example, a popular color format includes the red-green-blue (RGB) format having red, green, and blue channels. That is, in the RGB format, data of a pixel is represented by three numerical RGB components (Red, Green, Blue), that may be referred to as a channel data, to manipulate the color of pixel's area within the image. In some implementations, the three RGB components may be represented as three 8-bit numbers for each pixel. Three 8-bit bytes (one byte for each of RGB) may be used to generate 24-bit color. Each 8-bit RGB component can have 256 possible values, ranging from 0 to 255 (i.e., in the base 2 binary system, an 8-bit byte can contain one of 256 numeric values ranging from 0 to 255). This channel data (R, G, and B) can be assigned a value from 0 to 255 that can be used to set the pixel's color. For example, three values like (250, 165, 0), meaning (Red=250, Green=165, Blue=0), can denote one Orange pixel. As a further example, (Red=255, Green=255, Blue=0) means Red and Green, each fully saturated (255 is as bright as 8 bits can be), with no Blue (zero), with the resulting color being Yellow. As a still further example, the color black has an RGB value of (Red=0, Green=0, Blue=0) and white has an RGB value of (Red=255, Green=255, Blue=255). Gray has the property of having equal or similar RGB values, for example, (Red=220, Green=220, Blue=220) is a light gray (near white), and (Red=40, Green=40, Blue=40) is a dark gray (near black).

In this way, the composite of three RGB values creates a final color for a given pixel. With a 24-bit RGB color image, using 3 bytes to define a color, there can be 256 shades of red, and 256 shades of green, and 256 shades of blue. This provides 256×256×256, i.e., 16.7 million possible combinations or colors for 24 bit RGB color images. As such, a pixel's RGB data value indicates a degree of color or light each of a Red, a Green, and a Blue pixel is comprised of. The three colors, and their intensity levels, are combined at that image pixel, i.e., at that pixel location on a display screen, to illuminate a display screen at that location with that color. In is to be understood, however, that other bit sizes, having fewer or more bits, e.g., 10-bits, may be used to result in fewer or more overall colors and ranges.

As a whole, the various pixels, positioned together in a grid pattern (e.g., pixel data 202ap), form a digital image or portion thereof. A single digital image can comprise thousands or millions of pixels. Images can be captured, generated, stored, and/or transmitted in a number of formats, such as JPEG, TIFF, PNG and GIF. These formats use pixels to store or represent the image.

With reference to FIG. 2, example image 202a illustrates a scalp region of a user or individual. More specifically, image 202a comprises pixel data, including pixel data 202ap defining the scalp region of the user's or individual's scalp. Pixel data 202ap includes a plurality of pixels including pixel 202ap1, pixel 202ap2, and pixel 202ap3. In example image 202a, each of pixel 202ap1, pixel 202ap2, and pixel 202ap3 are each representative of features of scalp skin or hair follicle regions corresponding to image classifications of a scalp region. Generally, in various embodiments, features of the scalp skin or hair follicle regions of a user may comprise one or more of: (1) white sebum residue; (2) one or more lines of the scalp skin; (3) one or more cracks of the scalp skin; (4) one or more scalp plugs; and/or (5) scalp acne. Each of these features may be determined from or otherwise based on one or more pixels in a digital image (e.g., image 202a). For example, with respect to image 202a, each of pixels 202ap1, 202ap2, and 202ap3 may be relatively light pixels (e.g., pixels with relatively high L* values) and/or relatively yellow pixels (e.g., pixels with relatively high or positive b* values) positioned within pixel data 202ap in a scalp region of the user's scalp. Each of pixels 202ap1, 202ap2, and 202ap3 may be surrounded by darker and/or bluer (e.g., negative or lower relative b* values) pixels, indicating that each of pixels 202ap1, 202ap2, and 202ap3 is representative of a scalp plug at the location represented by each of the pixels 202ap1, 202ap2, and 202ap3 in the image 202a. Thus, the image 202a may receive a scalp plug image classification that classifies the represented scalp region as having one or more scalp plugs on the user's scalp.

In addition to pixels 202ap1, 202ap2, and 202ap3, pixel data 202ap includes various other pixels including remaining portions of the user's scalp, including various other scalp regions and/or portions of scalp skin or hair follicle regions that may be analyzed and/or used for training of model(s), and/or analysis by used of already trained models, such as scalp based learning model 108 as described herein. For example, pixel data 202ap further includes pixels representative of features of scalp skin or hair follicle regions corresponding to various image classifications, including, but not limited to (1) a white residue image classification (e.g., based on relative luminance (e.g., whiteness or L* value) of one or more pixels within pixel data 202ap), (2) a scalp plug image classification (e.g., as described for each of pixels 202ap1, 202ap2, and 202ap3), and/or (3) a scalp acne image classification (e.g., based on the redness (e.g., a* value) of one or more pixels within pixel data 202ap), and other classifications and/or features as shown in FIG. 2.

A digital image, such as a training image, an image as submitted by users, or otherwise a digital image (e.g., any of images 202a, 202b, and/or 202c), may be or may comprise a cropped image. Generally, a cropped image is an image with one or more pixels removed, deleted, or hidden from an originally captured image. For example, with reference to FIG. 2, image 202a represents an original image. Cropped portion 202ac1 represents a first cropped portion of image 202a that removes portions of the user's scalp (outside of cropped portion 202ac1) that may not include readily identifiable scalp skin or hair follicle region features. As a further example, cropped portion 202ac2 represents a second cropped portion of image 202a that removes portions of the image (outside of cropped portion 202ac2) that may not include scalp skin or hair follicle region features that are as readily identifiable as the features included in the cropped portion 202ac2, and may therefore be less useful as training data. In various embodiments, analyzing and/or use of cropped images for training yields improved accuracy of a scalp based learning model. It also improves the efficiency and performance of the underlying computer system in that such system processes, stores, and/or transfers smaller size digital images.

It is to be understood that the disclosure for image 202a of FIG. 2 applies the same or similarly for other digital images described herein, including, for example, images 202b and 202c, where such images also comprise pixels that may be analyzed and/or used for training of model(s) as described herein.

In addition, digital images of a scalp region of a user's scalp, as described herein, may depict various scalp skin and hair follicle region features, which may be used to train scalp based learning models across a variety of different users having a variety of different scalp skin and hair follicle region features. For example, as illustrated for images 202a, 202b, and 202c, the scalp regions of the users of these images comprise scalp skin and hair follicle region features of the user's scalp identifiable with the pixel data of the respective images. These scalp skin and hair follicle region features include, for example, one or more scalp plugs (e.g., as depicted in image 202a), white sebum residue and one or more lines/cracks of the scalp skin (e.g., as depicted in image 202b), and scalp acne (e.g., as depicted in image 202c).

Figure 3:
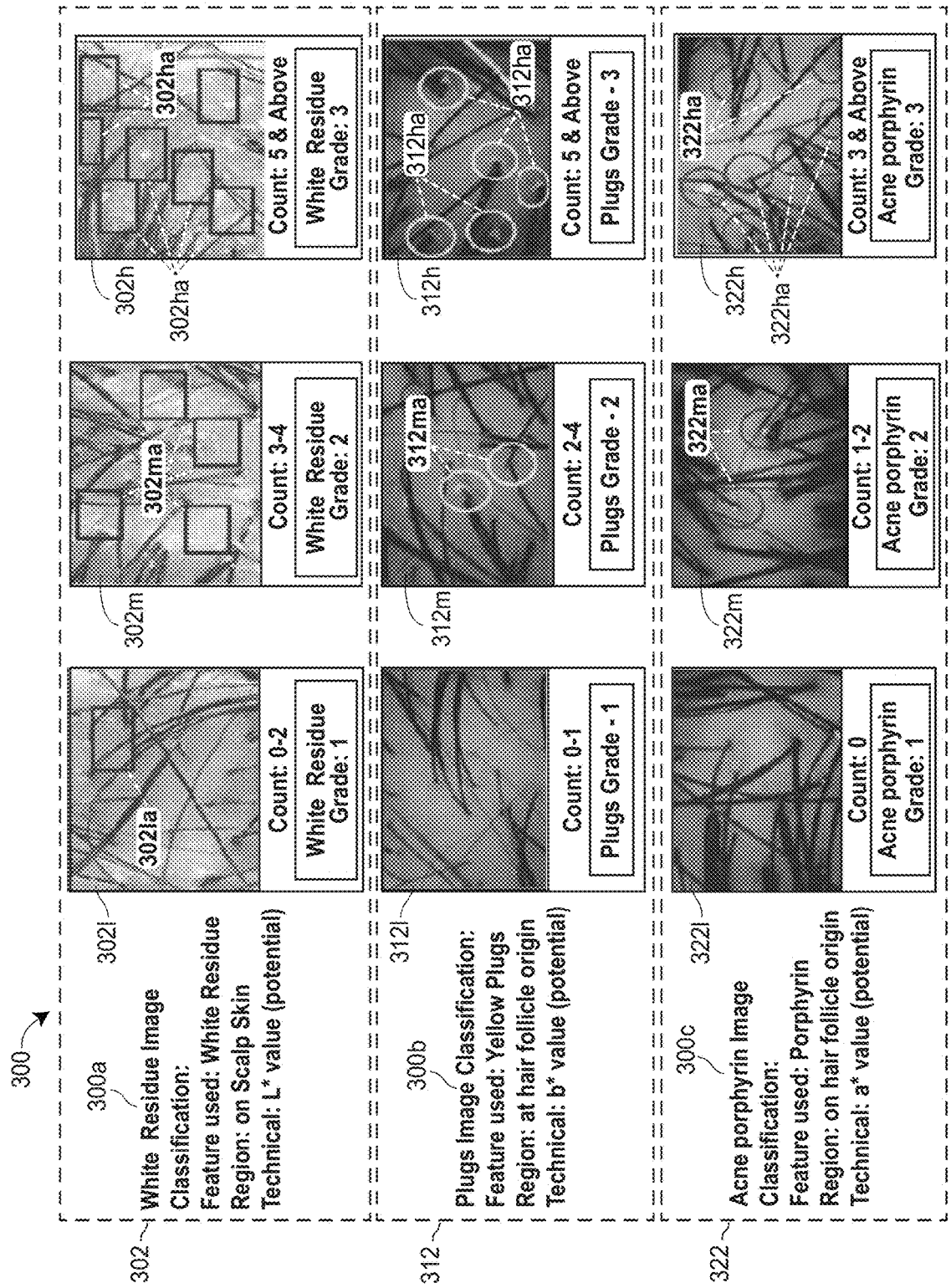
FIG. 3 illustrates an example set of scalp images having image classifications corresponding to features of scalp skin or hair follicle regions of respective individuals, in accordance with various embodiments disclosed herein.

In various embodiments, digital images (e.g., images 202a, 202b, and 202c), whether used as training images depicting individuals, or used as images depicting users or individuals for analysis and/or scalp classification, may comprise multiple angles or perspectives depicting scalp regions of each of the respective individual or the user. The multiple angles or perspectives may include different views, positions, closeness of the user and/or backgrounds, lighting conditions, or otherwise environments in which the user is positioned against in a given image. For example, FIG. 3 includes scalp images (e.g., 302l, 302m, 302h, 312l, 312m, 312h, 322l, 322m, and 322h) that depict scalp regions of respective individuals and/or users and are captured using different lighting conditions (e.g., visible, UV). More specifically, FIG. 3 illustrates an example set 300 of scalp images (302l, 302m, 302h, 312l, 312m, 312h, 322l, 322m, and 322h) having image classifications (e.g., 300a, 300b, and 300c) corresponding to features of scalp skin and/or hair follicle regions of respective individuals, in accordance with various embodiments disclosed herein. Such images maybe used for training a scalp based learning model, or for analysis, and/or user-specific scalp classifications, as described herein.

As shown in FIG. 3, scalp images (302l, 302m, 302h, 312l, 312m, 312h, 322l, 322m, and 322h) may comprise scalp cropped images, that is, images that have been cropped to include a scalp portion of a user or individual (e.g., as described herein for cropped portion 202ac2 of image 202a). In some embodiments, digital images, such as training images and/or images as provided by users or otherwise (e.g., any of images 202a, 202b, and/or 202c), may be or comprise cropped images depicting scalp skin and/or hair follicle regions with at least one or more features removed. Additionally, or alternatively, images may be sent as cropped or that otherwise include extracted or depicted scalp regions of a user without depicting personal identifiable information (PII) of the user. Such features provide a security improvement, i.e., where the removal of PII provides an improvement over prior systems because cropped or redacted images, especially ones that may be transmitted over a network (e.g., the Internet), are more secure without including PII information of a user. Importantly, the systems and methods described herein may operate without the need for such non-essential information, which provides an improvement, e.g., a security and a performance improvement, over conventional systems.

Moreover, while FIG. 3 may depict and describe cropped images, it is to be understood, however, that other image types including, but not limited to, original, non-cropped images (e.g., original image 202a) and/or other types/sizes of cropped images (e.g., cropped portion 202ac1 of image 202a) may be used or substituted as well.

With reference to FIG. 3, each of the images of image set 302 are classified, assigned, or otherwise identified as having a white residue image classification 300a. A "white residue" image classification indicates that a user's scalp skin or hair follicle region has feature(s) (e.g., identifiable within pixel data of a given image) indicating, for example, seborrheic dermatitis, dandruff, and/or other white scales, flakes, or crust on the scalp skin or hair follicle regions of the user's scalp. Determining that a given image classifies as a white residue image classification may include analyzing an image (and its related pixel data) that that is captured using a white light illumination source. It is to be understood that, additionally or alternatively, any suitable illumination source may be used, and more than one image of a scalp region or more than one scalp region of a user's scalp may be analyzed as well to determine the white residue image classification.

Each of the classifications described herein, including classifications corresponding to one or more features of scalp skin and hair follicle regions, may also include sub-classifications or different degrees of a given feature (e.g., white residue, scalp plugs, scalp acne, etc.) for a given classification. For example, with respect to image set 302, scalp image 302l has been classified, assigned, or has otherwise been identified as having a sub-classification or degree of "low white residue" (having a grade or value of white residue, corresponding to 1) indicating that the scalp image 302l, as determined from respective pixel data (e.g., L* values of pixel data included as part of image region 302la), indicates low or no white residue on the user's scalp, as depicted in the scalp image 302l. Likewise, scalp image 302m has been classified, assigned, or is otherwise identified as having a sub-classification or degree of "mid white residue" (having a grade or value of white residue, corresponding to 2) indicating that the scalp image 302m, as determined from respective pixel data (e.g., L* values of pixel data included as part of image regions collectively referenced as "302ma"), indicates a medium amount of white residue on the user's scalp, as depicted in the scalp image 302m. Finally, scalp image 302h has been classified, assigned, or is otherwise identified as having a sub-classification or degree of "high white residue" (having a grade or value of white residue, corresponding to 3) indicating that the scalp image 302h, as determined from respective pixel data (e.g., L* values of pixel data included as part of image regions collectively referenced as "302ha"), indicates a high amount of white residue on the user's scalp, as depicted in the scalp image 302h. Each of the images of image set 302, with their respective features indicating a specific classification (e.g., white residue image classification) and related sub-classifications or degrees, may be used to train or retrain a scalp based learning model (e.g., scalp based learning model 108) in order to make the scalp based learning model more accurate at detecting, determining, or predicting classifications and/or white residue based features (and, in various embodiments, degrees thereof) in images (e.g., user images 202a, 202b, and/or 202c) provided to the scalp based learning model.

With further reference to FIG. 3, each of the images of image set 312 have been classified, assigned, or otherwise identified as having a scalp plugs image classification 300b. A "scalp plugs" image classification indicates that a user's scalp skin or hair follicle regions has feature(s) (e.g., identifiable within pixel data of a given image) indicating scalp plugs (e.g., excess sebum deposits) on the scalp skin or hair follicle regions of the user's scalp. Determining that a given image classifies as a scalp plugs image classification may include analyzing an image (and its related pixel data, e.g., pixels 202ap1-3 of image 202a) that is captured using an ultraviolet (UV) illumination source to capture auto-fluorescence materials (e.g., scalp plugs). For example, scalp plugs may appear yellowish (e.g., scalp pixels may have positive b* values) in an image captured of a scalp region of a user's scalp if the image is captured using the UV illumination source. It is to be understood that, additionally or alternatively, other suitable illumination sources may be used, and more than one image of a scalp region or more than one scalp region of a user's scalp may be analyzed as well to determine the scalp plugs image classification.

With respect to image set 312, the scalp image 312l has been classified, assigned, or has otherwise been identified as having a sub-classification or degree of "low scalp plugs" (having a grade or value of scalp plugs, corresponding to 1) indicating that the scalp image 312l, as determined from respective pixel data, indicates low or no scalp plugs on the user's scalp, as depicted in the scalp image 312l. Likewise, the scalp image 312m has been classified, assigned, or is otherwise identified as having a sub-classification or degree of "mid scalp plugs" (having a grade or value of scalp plugs, corresponding to 2) indicating that the scalp image 312m, as determined from respective pixel data (e.g., b* values of pixel data included as part of image regions collectively referenced as "312ma"), indicates a medium amount of scalp plugs on the user's scalp, as depicted in the scalp image 312m. Finally, the scalp image 312h has been classified, assigned, or is otherwise identified as having a sub-classification or degree of "high scalp plugs" (having a grade or value of scalp plugs, corresponding to 3) indicating that the scalp image 312h, as determined from respective pixel data (e.g., b* values of pixel data included as part of image regions collectively referenced as "312ha"), indicates a high amount of scalp plugs on the user's scalp, as depicted in the scalp image 312h. Each of the images of image set 312, with their respective features indicating a specific classification (e.g., scalp plug image classification) and related sub-classifications or degrees, may be used to train or retrain a scalp based learning model (e.g., scalp based learning model 108) in order to make the scalp based learning model more accurate at detecting, determining, or predicting classifications and/or scalp plug based features (and, in various embodiments, degrees thereof) in images (e.g., user images 202a, 202b, and/or 202c) provided to the scalp based learning model.

With continued reference to FIG. 3, the images of image set 322 have been classified, assigned, or otherwise identified as having a scalp acne image classification 300c. A "scalp acne" image classification indicates that a user's scalp skin or hair follicle regions has feature(s) (e.g., identifiable within pixel data of a given image) indicating scalp acne on the scalp skin or hair follicle regions of the user's scalp. Determining that a given image classifies as a scalp acne image classification may include analyzing an image (and its related pixel data) that is captured using an UV illumination source to capture auto-fluorescence materials (e.g., scalp acne). For example, scalp acne may appear reddish (e.g., scalp acne pixels may have positive a* values) in an image captured of a scalp region of a user's scalp if the image is captured using the UV illumination source. It is to be understood that, additionally or alternatively, other suitable illumination sources may be used, and more than one image of a scalp region or more than one scalp region of a user's scalp may be analyzed as well to determine the scalp plugs image classification.

With respect to image set 322, the scalp image 322*l* has been classified, assigned, or has otherwise been identified as having a sub-classification or degree of "low scalp acne" (having a grade or value of scalp acne, corresponding to 1) indicating that the scalp image 322*l*, as determined from respective pixel data, indicates low or no scalp acne on the user's scalp, as depicted in the scalp image 322*l*. Likewise, the scalp image 322*m* has been classified, assigned, or is otherwise identified as having a sub-classification or degree of "mid scalp acne" (having a grade or value of scalp acne, corresponding to 2) indicating that the scalp image 322*m*, as determined from respective pixel data (e.g., a* values of pixel data included as part of image regions collectively referenced as "322*ma*"), indicates a medium amount of scalp acne on the user's scalp, as depicted in the scalp image 322*m*. Finally, the scalp image 322*h* has been classified, assigned, or is otherwise identified as having a sub-classification or degree of "high scalp acne" (having a grade or value of scalp acne, corresponding to 3) indicating that the scalp image 322*h*, as determined from respective pixel data (e.g., a* values of pixel data included as part of image regions collectively referenced as "322*ha*"), indicates a high amount of scalp acne on the user's scalp, as depicted in the scalp image 322*h*. Each of the images of image set 322, with their respective features indicating a specific classification (e.g., scalp acne image classification) and related sub-classifications or degrees, may be used to train or retrain a scalp based learning model (e.g., scalp based learning model 108) in order to make the scalp based learning model more accurate at detecting, determining, or predicting classifications and/or scalp acne based features (and, in various embodiments, degrees thereof) in images (e.g., user images 202*a*, 202*b*, and/or 202*c*) provided to the scalp based learning model.

While FIG. 3 illustrates three image classifications for image features, including white residue, scalp plugs, and scalp acne, it is to be understood that additional classifications (e.g., such as scalp skin cracks/lines) are similarly contemplated herein. In addition, the various classifications may be used together, where a single image may be classified as having, or being otherwise identified with, multiple image classifications. For example, in various embodiments, computing instructions may further cause one or more processors (e.g., of server(s) 102 and/or a user computing device) to analyze, by a scalp based learning model, an image captured by the imaging device to determine a second image classification of a user's scalp region as selected from one or more image classifications of the scalp based learning model. A user-specific scalp classification, as described herein, may further based on the second image classification of the user's scalp region. Third, fourth, etc. image classifications may also be assigned and/or used for a given image, as well.

Figure 4:
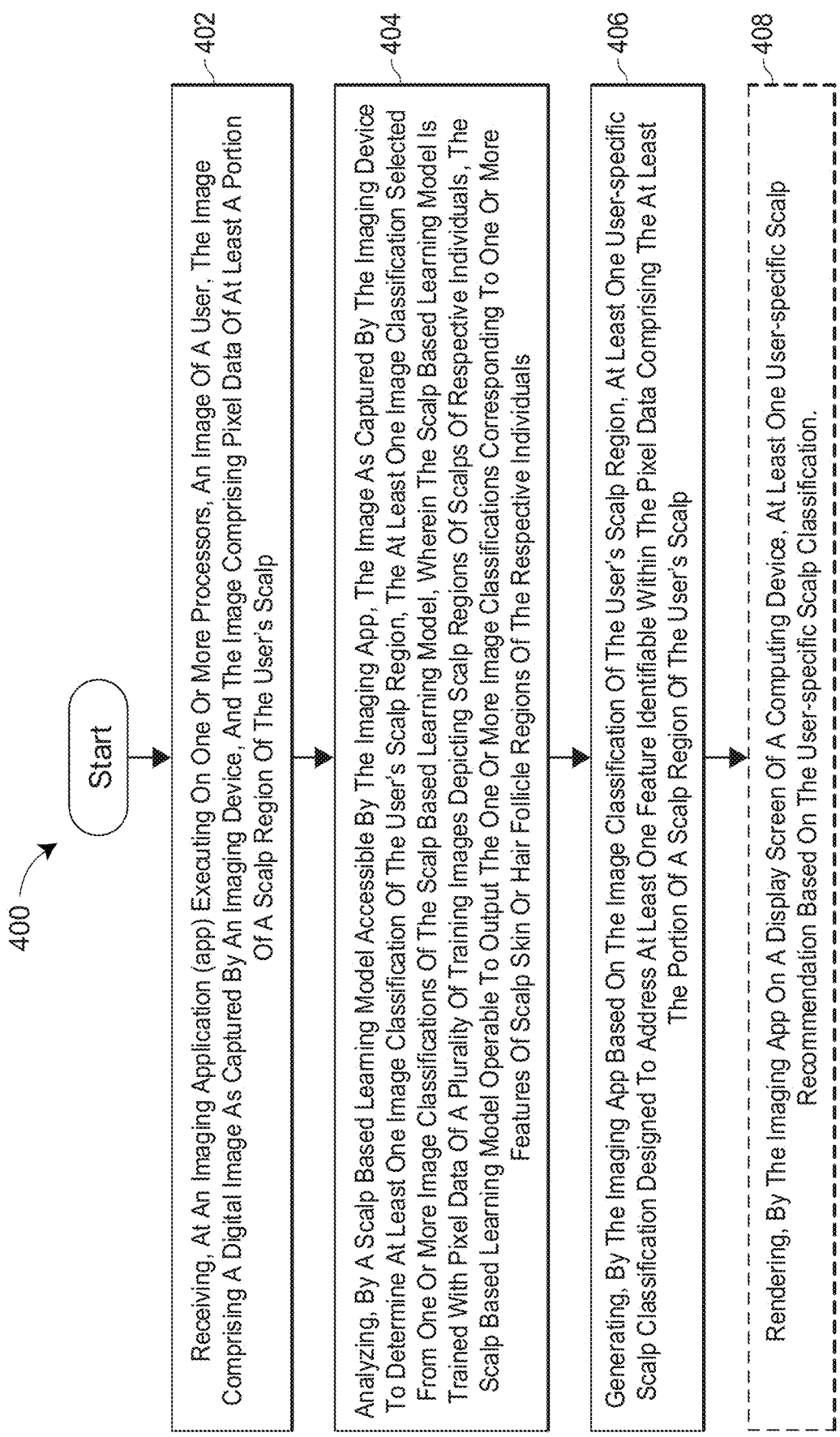
FIG. 4 illustrates a digital imaging and learning method for analyzing pixel data of an image of a scalp region of a user's scalp to generate one or more user-specific scalp classifications, in accordance with various embodiments disclosed herein.

FIG. 4 illustrates a digital imaging and learning method 400 for analyzing pixel data of an image (e.g., any of images 202*a*, 202*b*, and/or 202*c*; and/or scalp images (302*l*, 302*m*, 302*h*, 312*l*, 312*m*, 312*h*, 322*l*, 322*m*, and/or 322*h*)) of a scalp region of a user's scalp to generate one or more user-specific scalp classifications, in accordance with various embodiments disclosed herein. Images, as used with the method 400, and more generally as described herein, are pixel based images as captured by an imaging device (e.g., an imaging device of user computing device 111*c*1). In some embodiments an image may comprise or refer to a plurality of images such as a plurality of images (e.g., frames) as collected using a digital video camera. Frames comprise consecutive images defining motion, and can comprise a movie, a video, or the like.

At block 402, the method 400 comprises receiving, at an imaging application (app) executing on one or more processors (e.g., one or more processor(s) 104 of server(s) 102 and/or processors of a computer user device, such as a mobile device), an image of a user. The image may comprise a digital image as captured by an imaging device (e.g., an imaging device of user computing device 111*c*1 or 112*c*4). The image may comprise pixel data of at least a portion of a scalp region of the user's scalp. Particularly, in certain aspects, the scalp region of the user's scalp may include at least one of (i) a frontal scalp region, (ii) a mid-center scalp region, (iii) a custom defined scalp region, and/or other suitable scalp regions or combinations thereof.

In certain aspects, the one or more processors may comprise a processor of a mobile device, which may include at least one of a handheld device (e.g., user computing device 111*c*1) or a portable microscope (e.g., portable microscope device 112*c*4). Accordingly, in these aspects, the imaging device may comprise a digital camera of the mobile device. For example, if the imaging device is a portable microscope (e.g., portable microscope device 112*c*4), the user may capture images of the user's scalp region using the camera of the portable microscope, and the portable microscope may process/analyze the captured images using the one or more processors of the portable microscope and/or may transmit the captured images to a connected mobile device (e.g., user computing device 112*c*1) for processing/analysis, in accordance with the actions of the method 400 described herein.

At block 404, the method 400 comprises analyzing, by a scalp based learning model (e.g., scalp based learning model 108) accessible by the imaging app, the image as captured by the imaging device to determine at least one image classification of the user's scalp region. The at least one image classification is selected from one or more image classifications (e.g., any one or more of white residue image classification 300*a*, scalp plugs image classification 300*b*, and/or scalp acne image classification 300*c*) of the scalp based learning model.

A scalp based learning model (e.g., scalp based learning model 108) as referred to herein in various embodiments, is trained with pixel data of a plurality of training images (e.g., any of images 202*a*, 202*b*, and/or 202*c*; rear scalp images (302*l*, 302*m*, 302*h*, 312*l*, 312*m*, 312*h*, 322*l*, 322*m*, and/or 322*h*; and/or front scalp images (352*l*, 352*m*, 352*h*, 362*l*, 362*m*, 362*h*, 372*l*, 372*m*, and/or 372*h*) depicting scalp regions of scalps of respective individuals. The scalp based learning model is configured to, or is otherwise operable to, output the one or more image classifications corresponding to one or more features of scalp skin or hair follicle regions of respective individuals. In various embodiments, one or more of the plurality of training images or the at least one image of the user each include at least one cropped image depicting the scalp having a single instance of a scalp skin feature or a hair follicle feature. Further, in various embodiments, the one or more of the plurality of training images or the at least one image of the user comprise multiple angles or perspectives depicting scalp regions of the respective individuals or the user.

In various embodiments, the one or more image classifications determined by the scalp based learning model (e.g., scalp based learning model 108) may include one or more of (1) a white residue image classification, (2) a scalp plug image classification, and/or (3) a scalp acne image classification. In various embodiments, the scalp region of the user includes scalp skin having one or more scalp skin features identifiable within the pixel data, and the one or more scalp skin features may include one or more of: (1) white sebum residue; (2) one or more lines of the scalp skin; and/or (3) one or more cracks of the scalp skin. In various embodiments, the scalp region of the user includes hair follicle regions having one or more hair follicle features identifiable within the pixel data, and the one or more hair follicle features may include one or more of: (1) one or more scalp plugs; and/or (2) scalp acne.

In various embodiments, the scalp based learning model (e.g., scalp based learning model 108) is an artificial intelligence (AI) based model trained with at least one AI algorithm. Training of the scalp based learning model 108 involves image analysis of the training images to configure weights of the scalp based learning model 108, and its underlying algorithm (e.g., machine learning or artificial intelligence algorithm) used to predict and/or classify future images. For example, in various embodiments herein, generation of the scalp based learning model 108 involves training the scalp based learning model 108 with the plurality of training images of a plurality of individuals, where each of the training images comprise pixel data and depict scalp regions of scalps of respective individuals. In some embodiments, one or more processors of a server or a cloud-based computing platform (e.g., imaging server(s) 102) may receive the plurality of training images of the plurality of individuals via a computer network (e.g., computer network 120). In such embodiments, the server and/or the cloud-based computing platform may train the scalp based learning model with the pixel data of the plurality of training images.

In various embodiments, a machine learning imaging model, as described herein (e.g. scalp based learning model 108), may be trained using a supervised or unsupervised machine learning program or algorithm. The machine learning program or algorithm may employ a neural network, which may be a convolutional neural network, a deep learning neural network, or a combined learning module or program that learns in two or more features or feature datasets (e.g., pixel data) in a particular areas of interest. The machine learning programs or algorithms may also include natural language processing, semantic analysis, automatic reasoning, regression analysis, support vector machine (SVM) analysis, decision tree analysis, random forest analysis, K-Nearest neighbor analysis, naïve B ayes analysis, clustering, reinforcement learning, and/or other machine learning algorithms and/or techniques. In some embodiments, the artificial intelligence and/or machine learning based algorithms may be included as a library or package executed on imaging server(s) 102. For example, libraries may include the TENSORFLOW based library, the PYTORCH library, and/or the SCIKIT-LEARN Python library.

Machine learning may involve identifying and recognizing patterns in existing data (such as identifying features of scalp skin, hair follicle regions, and/or other scalp related features in the pixel data of image as described herein) in order to facilitate making predictions or identification for subsequent data (such as using the model on new pixel data of a new image in order to determine or generate a user-specific scalp classification designed to address at least one feature identifiable within the pixel data comprising the at least the portion of a scalp region of the user's scalp).

Machine learning model(s), such as the scalp based learning model described herein for some embodiments, may be created and trained based upon example data (e.g., "training data" and related pixel data) inputs or data (which may be termed "features" and "labels") in order to make valid and reliable predictions for new inputs, such as testing level or production level data or inputs. In supervised machine learning, a machine learning program operating on a server, computing device, or otherwise processor(s), may be provided with example inputs (e.g., "features") and their associated, or observed, outputs (e.g., "labels") in order for the machine learning program or algorithm to determine or discover rules, relationships, patterns, or otherwise machine learning "models" that map such inputs (e.g., "features") to the outputs (e.g., labels), for example, by determining and/or assigning weights or other metrics to the model across its various feature categories. Such rules, relationships, or otherwise models may then be provided subsequent inputs in order for the model, executing on the server, computing device, or otherwise processor(s), to predict, based on the discovered rules, relationships, or model, an expected output.

In unsupervised machine learning, the server, computing device, or otherwise processor(s), may be required to find its own structure in unlabeled example inputs, where, for example multiple training iterations are executed by the server, computing device, or otherwise processor(s) to train multiple generations of models until a satisfactory model, e.g., a model that provides sufficient prediction accuracy when given test level or production level data or inputs, is generated.

Supervised learning and/or unsupervised machine learning may also comprise retraining, relearning, or otherwise updating models with new, or different, information, which may include information received, ingested, generated, or otherwise used over time. The disclosures herein may use one or both of such supervised or unsupervised machine learning techniques.

In various embodiments, a scalp based learning model (e.g., scalp based learning model 108) may be trained, by one or more processors (e.g., one or more processor(s) 104 of server(s) 102 and/or processors of a computer user device, such as a mobile device) with the pixel data of a plurality of training images (e.g., any of images 202a, 202b, and/or 202c; and/or scalp images 302*l*, 302*m*, 302*h*, 312*l*, 312*m*, 312*h*, 322*l*, 322*m*, and/or 322*h*). In various embodiments, a scalp based learning model (e.g., scalp based learning model 108) is configured to output one or more features of scalp skin or hair follicle regions for each of the plurality of training images. In these embodiments, the one or more features of scalp skin or hair follicle regions may differ based on one or more user demographics and/or ethnicities of the respective individuals represented in the respective training images, e.g., as typically associated with, or otherwise naturally occurring for, different races, genomes, and/or geographic locations associated with such demographics and/or ethnicities. Still further, the scalp based learning model (e.g., scalp based learning model 108) may generate a user-specific scalp classification of each respective individual represented in the respective training images based on the ethnicity and/or demographic value of the respective individual.

In various embodiments, image analysis may include training a machine learning based model (e.g., the scalp based learning model 108) on pixel data of images depicting scalp regions of scalps of respective individuals. Additionally, or alternatively, image analysis may include using a machine learning imaging model, as previously trained, to determine, based on the pixel data (e.g., including their L*, a*, and b* values) one or more images of the individual(s), an image classification of the user's scalp region. The weights of the model may be trained via analysis of various L*a*b* values of individual pixels of a given image. For example, dark or low L* values (e.g., a pixel with an L* value less than 50) may indicate regions of an image where hair is present or where scalp lines/cracks are present. Likewise, a slightly lighter L* values (e.g., a pixel with an L* value greater than 50) may indicate the presence of white residue on the user's scalp. Still further, high/low a* values may indicate areas of the scalp containing more/less scalp acne, and high/low b* values may indicate areas of the scalp containing more/less scalp plugs. Together, when a pixel having scalp toned L*a*b* values is positioned within a given image, or is otherwise surrounded by, a group or set of pixels having scalp/hair toned colors, then a scalp based learning model (e.g., scalp based learning model 108) can determine an image classification of a user's scalp region, as identified within the given image. In this way, pixel data (e.g., detailing scalp regions of scalps of respective individuals) of 10,000s training images may be used to train or use a machine learning imaging model to determine an image classification of the user's scalp region.

In various embodiments, the scalp based learning model 108 may be an ensemble model comprising multiple models or sub-models that are configured to operate together. For example, in some embodiments, each scalp model be trained to identify or predict an image classification for a given image, where each scalp model may output or determine a classification for an image such that a given image may be identified, assigned, determined, or classified with one or more image classifications. Namely, the scalp based learning model 108 may include a first scalp model configured to determine a white residue image classification, a second scalp model configured to determine a scalp plugs image classification, a third scalp model configured to determine a scalp acne image classification, and/or any other suitable scalp model configured to determine any suitable additional image classifications or combinations thereof. In these embodiments, the user-specific scalp classification, as discussed further herein, may be based on each of the image classifications determined for the given image of the user's scalp region.

Continuing the above example, each scalp model included as part of the ensemble model may have a network architecture comprising an Efficient Net architecture. Generally, an Efficient Net is a convolutional neural network (CNN) architecture comprising a scaling algorithm that uniformly scales all dimensions of an image (e.g., depth, width, resolution of a digital image) using a compound coefficient. That is, the Efficient Net scaling algorithm uniformly scales a model's network values (e.g., a model's weights values), such as a model's width, depth, and resolution values, with a set of fixed scaling coefficients. The coefficients can be adjusted to adapt the efficiency of a given network architecture, and, therefore, the efficiency or impact of the underlying computing system (e.g., imaging server(s) 102 and/or user computing device, e.g., 111c1). For example, to decrease computational resources by $2^N$, as used by an underlying computing system, a network architecture's depth may be decreased by $\alpha^N$, its width may be decreased by $\beta^N$, and its image size may be decreased by $\gamma^N$, where each of $\alpha$, $\beta$, and $\gamma$ are constant coefficients applied to the network architecture, and may be determined, e.g., by a grid search or review of an original model.

In various embodiments, an Efficient Net architecture (e.g., of any of the models included as part of the ensemble model) may use a compound coefficient $\phi$ to uniformly scale each of network width, depth, and resolution in a principled way. In such embodiments, compound scaling may be used based on image size, where, e.g., larger images may require a network of a model to have more layers to increase the receptive field and more channels (e.g., L*a*b* channels of a pixel) to capture fine-grained patterns within a larger image comprising more pixels.

In any event, the scalp models may provide multi-class classification (e.g., an ensemble model), of scalp skin and/or hair follicle region attributes (e.g. white residue, scalp plugs, and scalp acne). In this example, the ensemble model may be trained with hundreds of scalp images (e.g., images 302*l*, 302*m*, 302*h*, 312*l*, 312*m*, 312*h*, 322*l*, 322*m*, and/or 322*h*). Moreover, following training, each of the scalp models may achieve high accuracy when identifying each corresponding attribute/feature. For example, the white residue scalp model may achieve approximately 77% accuracy when identifying, classifying, determining, and/or assigning a white residue image classification. The scalp plugs scalp model may achieve approximately 70% accuracy when identifying, classifying, determining, and/or assigning a scalp plugs image classification. The scalp acne scalp model may achieve approximately 79% accuracy when identifying, classifying, determining, and/or assigning a scalp acne image classification.

Although the prior example uses Efficient Net models and architectures, it is to be understood, however, that other AI model architectures and/or types, such as other types of CNN architectures, may be used instead of Efficient Net architectures. In addition, while an ensemble model or multi-class model is shown, it is to be understood that a one or more models may be used, including a single model based on a single AI model, such as a single Efficient Net neural network architecture or other AI algorithm.

At block 406, the method 400 comprises generating, by the imaging app based on the image classification of the user's scalp region, at least one user-specific scalp classification. The user-specific scalp classification is generated or designed to address at least one feature identifiable within the pixel data comprising the at least the portion of a scalp region of the user's scalp. In various embodiments, computing instructions of the imaging app when executed by one or more processors, may cause the one or more processors to generate a scalp quality code as determined based on the user-specific scalp classification designed to address the at least one feature identifiable within the pixel data comprising the at least the portion of a scalp region of the user's scalp. These scalp quality codes may include a LAP based code, a beauty code, and/or any other suitable code. For example, in these embodiments, the user-specific scalp classification may include an average/sum value corresponding to the respective scores/values associated with each feature/attribute analyzed as part of the scalp based learning model (e.g., scalp based learning model 108).

To illustrate, if a user receives low scores for each of the white residue image classification, the scalp plugs image classification, and/or the scalp acne image classification (e.g., 1 for each image classification), then the user may receive a user-specific scalp classification of "good" or "healthy." By contrast, if a user receives high scores for each of the white residue image classification, the scalp plugs image classification, and/or the scalp acne image classification (e.g., 3 for each image classification), then the user may receive a user-specific scalp classification of "bad" or "unhealthy."

In various embodiments, computing instructions of the imaging app may further cause one or more processors to record the image of the user as captured by the imaging device at a first time for tracking changes to user's scalp region over time. The computing instructions may also cause the one or more processors to record the image of the user in one or more memories communicatively coupled to the one or more processors. Further, the computing instructions may cause the one or more processors to receive a second image of the user that is captured by the imaging device at a second time. The second image may include pixel data of at least a portion of a scalp region of the user's scalp. The computing instructions may also cause the one or more processors to analyze, by the scalp based learning model, the second image captured by the imaging device to determine, at the second time, a second image classification of the user's scalp region as selected from the one or more image classifications of the scalp based learning model. The computing instructions may also cause the one or more processors to generate, based on a comparison of the image and the second image or the classification or the second classification of the user's scalp region, a new user-specific scalp classification regarding at least one feature identifiable within the pixel data of the second image comprising the at least the portion of a scalp region of the user's scalp.

In various embodiments, one or more processors configured to execute computing instructions comprising the imaging app may comprise a server processor of a server. The server may be communicatively coupled to a computing device via a computer network, and the imaging app may comprise a server app portion configured to execute on the one or more processors of the server and a computing device app portion configured to execute on one or more processors of the computing device. The server app portion may be configured to communicate with the computing device app portion, and the server app portion may be configured to implement one or more of: (1) receiving the image captured by the imaging device; (2); determining the at least one image classification of the user's scalp region; (3) generating the user-specific scalp classification; or (4) transmitting a user-specific recommendation the computing device app portion.

With reference to FIG. 4, at optional block 408, the method 400 comprises rendering, by the imaging app on a display screen of a computing device (e.g., user computing device 111c1), at least one user-specific scalp recommendation that is based on the user-specific scalp classification. In various embodiments, the at least one user-specific scalp recommendation is displayed on the display screen of the computing device with instructions for treating the at least one feature identifiable in the pixel data comprising the at least the portion of the scalp region of the user's scalp.

The user-specific scalp recommendation may be generated by a user computing device (e.g., user computing device 111c1) and/or by a server (e.g., imaging server(s) 102). For example, in some embodiments imaging server(s) 102, as described herein for FIG. 1, may analyze a user image remote from a user computing device to determine an image classification of the user's scalp region, the user-specific scalp classification designed to address at least one feature identifiable within the pixel data comprising the at least the portion of a scalp region of the user's scalp, and/or the user-specific scalp recommendation. For example, in such embodiments imaging server or a cloud-based computing platform (e.g., imaging server(s) 102) receives, across computer network 120, the at least one image comprising the pixel data of at the least a portion of a scalp region of the user's scalp. The server or a cloud-based computing platform may then execute scalp based learning model (e.g., scalp based learning model 108) and generate, based on output of the scalp based learning model (e.g., scalp based learning model 108), the user-specific scalp recommendation. The server or a cloud-based computing platform may then transmit, via the computer network (e.g., computer network 120), the user-specific scalp recommendation to the user computing device for rendering on the display screen of the user computing device. For example, and in various embodiments, the at least one user-specific scalp recommendation may be rendered on the display screen of the user computing device in real-time or near-real time, during, or after receiving, the image having the scalp region of the user's scalp.

As an example, in various embodiments, the user-specific scalp recommendation may include a recommended wash frequency specific to the user. The recommended wash frequency may comprise a number of times to wash, one or more times or periods over a day, week, etc. to wash, suggestions as to how to wash, etc. Moreover, in various embodiments, the user-specific scalp recommendation may comprise a textual recommendation, a visual/image based recommendation, and/or a virtual rendering of the at least the portion of the scalp region of the user's scalp, e.g., displayed on the display screen of a user computing device (e.g., user computing device 111c1). Such scalp classification may include a graphical representation of the user's scalp as annotated with one or more graphics or textual renderings corresponding to user-specific attributes (e.g., white residue, scalp plugs, scalp acne, etc.).

Further, in embodiments including a new user-specific scalp classification, one or more processors (e.g., imaging server(s) 102 and/or a user computing device, such as user computing device 111c1) may render, on a display screen of a computing device, the new user-specific scalp classification and/or a new user-specific scalp recommendation. For example, if the new user-specific classification indicates that the user's scalp health has improved in the time between the first image capture and the second image capture, the one or more processors may highlight or otherwise indicate specific areas of improvement within the second image (e.g., specific areas previously identified within the first image as including white residue, scalp plugs, and/or scalp acne) and the new user-specific scalp classification may indicate "improved," and/or any suitable indication. Moreover, the one or more processors may render a new user-specific scalp recommendation that includes a recommendation to improve the user's scalp health based upon the new user-specific scalp classification.

In additional embodiments, the at least one user-specific scalp classification may comprise a product recommendation for a manufactured product. Additionally, or alternatively, in some embodiments, the at least one user-specific scalp classification may be displayed on the display screen of a computing device (e.g., user computing device 111c1) with instructions (e.g., a message) for treating, with the manufactured product, the at least one feature identifiable in the pixel data comprising the at least the portion of a scalp region of the user's scalp. In still further embodiments, computing instructions, executing on processor(s) of either a user computing device (e.g., user computing device 111c1) and/or imaging server(s) may initiate, based on the at least one user-specific scalp recommendation, the manufactured product for shipment to the user.

With regard to manufactured product recommendations, in some embodiments, one or more processors (e.g., imaging server(s) 102 and/or a user computing device, such as user computing device 111c1) may generate a modified image based on the at least one image of the user, e.g., as originally received. In such embodiments, the modified image may depict a rendering of how the user's scalp skin or hair follicle regions are predicted to appear after treating the at least one feature with the manufactured product. For example, the modified image may be modified by updating, smoothing, or changing colors of the pixels of the image to represent a possible or predicted change after treatment of the at least one feature within the pixel data with the manufactured product. The modified image may then be rendered on the display screen of the user computing device (e.g., user computing device 111c1).

Figure 5:
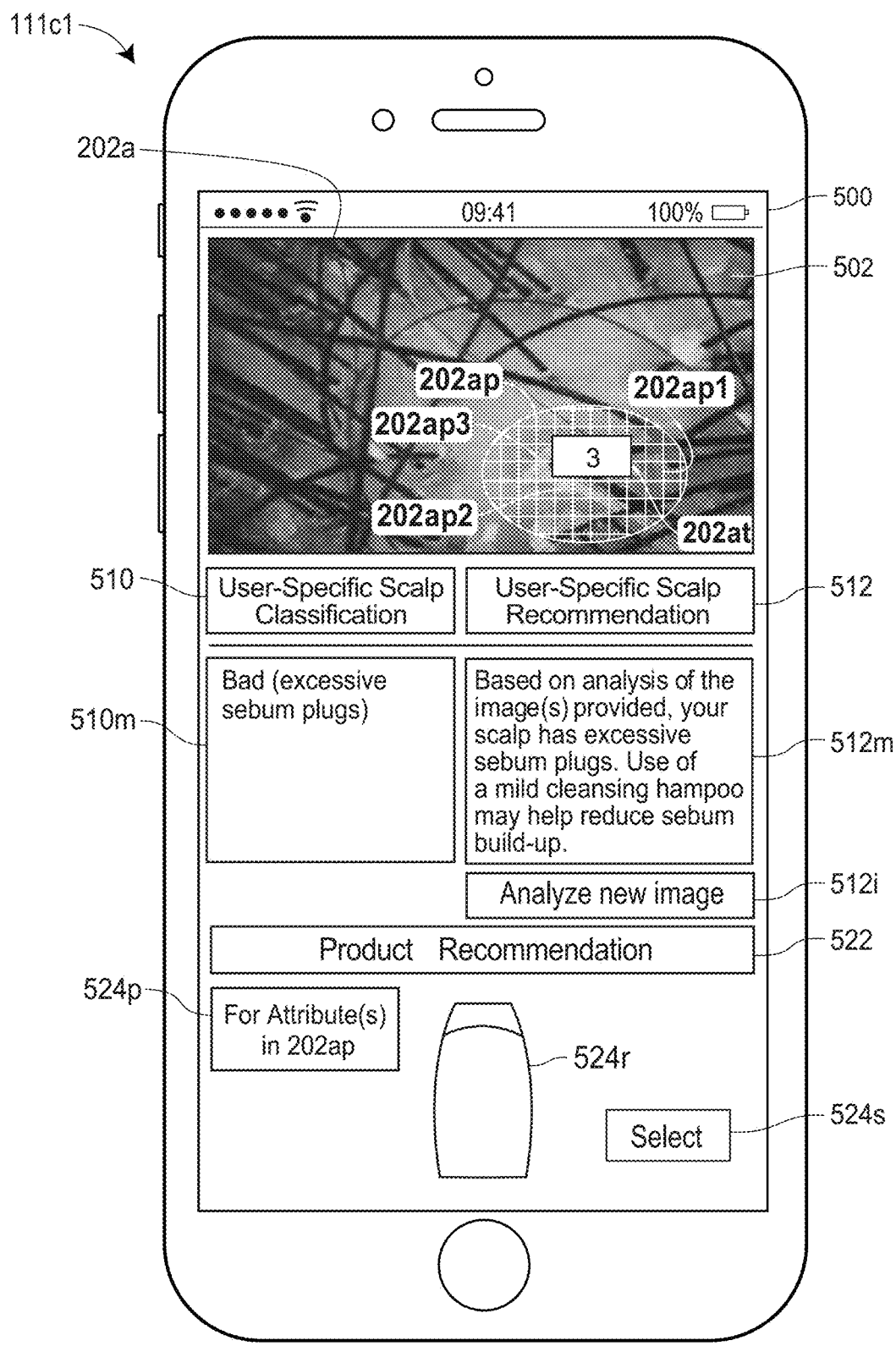
FIG. 5 illustrates an example user interface as rendered on a display screen of a user computing device in accordance with various embodiments disclosed herein.

FIG. 5 illustrates an example user interface 502 as rendered on a display screen 500 of a user computing device (e.g., user computing device 111c1) in accordance with various embodiments disclosed herein. For example, as shown in the example of FIG. 5, user interface 502 may be implemented or rendered via an application (app) executing on user computing device 111c1. For example, as shown in the example of FIG. 5, user interface 502 may be implemented or rendered via a native app executing on user computing device 111c1. In the example of FIG. 5, user computing device 111c1 is a user computer device as described for FIG. 1, e.g., where 111c1 is illustrated as an APPLE iPhone that implements the APPLE iOS operating system and that has display screen 500. User computing device 111c1 may execute one or more native applications (apps) on its operating system, including, for example, imaging app as described herein. Such native apps may be implemented or coded (e.g., as computing instructions) in a computing language (e.g., SWIFT) executable by the user computing device operating system (e.g., APPLE iOS) by the processor of user computing device 111c1.

Additionally, or alternatively, user interface 502 may be implemented or rendered via a web interface, such as via a web browser application, e.g., Safari and/or Google Chrome app(s), or other such web browser or the like.

As shown in the example of FIG. 5, user interface 502 comprises a graphical representation (e.g., of image 202a) of a user's scalp. Image 202a may comprise the image of the user (or graphical representation thereof) comprising pixel data (e.g., pixel data 202ap) of at least a portion of a scalp region of the user's scalp as described herein. In the example of FIG. 5, graphical representation (e.g., image 202a) of the user is annotated with one or more graphics (e.g., areas of pixel data 202ap) or textual rendering(s) (e.g., text 202at) corresponding to various features identifiable within the pixel data comprising a portion of a scalp region of the user's scalp. For example, the area of pixel data 202ap may be annotated or overlaid on top of the image of the user (e.g., image 202a) to highlight the area or feature(s) identified within the pixel data (e.g., feature data and/or raw pixel data) by the scalp based learning model (e.g., scalp based learning model 108). In the example of FIG. 5, the area of pixel data 202ap indicates features, as defined in pixel data 202ap, including scalp plugs (e.g., for pixels 202ap1-3), and may indicate other features shown in area of pixel data 202ap (e.g., white residue, scalp acne, scalp skin lines/cracks, etc.), as described herein. In various embodiments, the pixels identified as the specific features (e.g., pixels 202ap1-3), may be highlighted or otherwise annotated when rendered on display screen 500.

Textual rendering (e.g., text 202at) shows a user-specific attribute or feature (e.g., 3 for pixels 202ap1-3) which indicates that the user has a scalp quality score (of 3) for scalp plugs. The 3 score indicates that the user has a high scalp plugs scalp quality score, such that the user would likely benefit from washing their scalp with a mild shampoo to improve their scalp health/quality (e.g., reduce the number of scalp plugs). It is to be understood that other textual rendering types or values are contemplated herein, where textual rendering types or values may be rendered, for example, such as scalp quality scores for white residue, scalp plugs, scalp acne, scalp skin lines/cracks, or the like. Additionally, or alternatively, color values may be used and/or overlaid on a graphical representation shown on user interface 502 (e.g., image 202a) to indicate a degree or quality of a given scalp quality score, e.g., a high score of 3 or a low score of 1 (e.g., scores as shown in FIG. 3), or otherwise. The scores may be provided as raw scores, absolute scores, percentage based, scores. Additionally, or alternatively, such scores may be presented with textual or graphical indicators indicating whether or not a score is representative of positive results (good scalp washing frequency), negative results (poor scalp washing frequency), or acceptable results (average or acceptable scalp washing frequencies).

User interface 502 may also include or render a user-specific scalp classification 510. In the embodiment of FIG. 5, the user-specific scalp classification 510 comprises a message 510m to the user designed to indicate the user-specific scalp classification to the user, along with a brief description of any reasons resulting in the user-specific scalp classification. As shown in the example of FIG. 5, message 512m indicates to a user that the user-specific scalp classification is "Bad" and further indicates to the user that the user-specific scalp classification results from the scalp region of the user's scalp containing "excessive sebum plugs."

User interface 502 may also include or render a user-specific scalp recommendation 512. In the embodiment of FIG. 5, user-specific scalp recommendation 512 comprises a message 512m to the user designed to address at least one feature identifiable within the pixel data comprising the portion of a scalp region of the user's scalp. As shown in the example of FIG. 5, message 512m recommends to the user to wash their scalp to improve their scalp health/quality by reducing excess sebum build-up.

Message 512m further recommends use of a mild shampoo to help reduce the excess sebum build-up. The mild shampoo recommendation can be made based on the high scalp quality score for scalp plugs (e.g., 3) suggesting that the image of the user depicts a high number of scalp plugs, where the mild shampoo product is designed to address scalp plugs detected or classified in the pixel data of image 202a or otherwise assumed based on the high scalp quality score, or classification, for scalp plugs. The product recommendation can be correlated to the identified feature within the pixel data, and the user computing device 111c1 and/or server(s) 102 can be instructed to output the product recommendation when the feature (e.g., excessive sebum (scalp) plugs) is identified or classified (e.g., scalp plugs image classification 300b).

User interface 502 may also include or render a section for a product recommendation 522 for a manufactured product 524r (e.g., mild shampoo as described above). The product recommendation 522 may correspond to the user-specific scalp recommendation 512, as described above. For example, in the example of FIG. 5, the user-specific scalp recommendation 512 may be displayed on display screen 500 of user computing device 111c1 with instructions (e.g., message 512m) for treating, with the manufactured product (manufactured product 524r (e.g., mild shampoo)) at least one feature (e.g., high scalp quality score of 3 related to scalp plugs at pixels 202ap1-3) identifiable in the pixel data (e.g., pixel data 202ap) comprising pixel data of at least a portion of a scalp region of the user's scalp.

As shown in FIG. 5, user interface 502 recommends a product (e.g., manufactured product 524r (e.g., mild shampoo)) based on the user-specific scalp recommendation 512. In the example of FIG. 5, the output or analysis of image(s) (e.g. image 202a) of scalp based learning model (e.g., scalp based learning model 108), e.g., user-specific scalp classification 510 and/or its related values (e.g., 3 scalp plugs quality score) or related pixel data (e.g., 202ap1, 202ap2, and/or 202ap3), and/or the user-specific scalp recommendation 512, may be used to generate or identify recommendations for corresponding product(s). Such recommendations may include products such as shampoo, conditioner, hair gel, moisturizing treatments, and the like to address the user-specific issue as detected within the pixel data by the scalp based learning model (e.g., scalp based learning model 108).

In the example of FIG. 5, user interface 502 renders or provides a recommended product (e.g., manufactured product 524r) as determined by scalp based learning model (e.g., scalp based learning model 108) and its related image analysis of image 202a and its pixel data and various features. In the example of FIG. 5, this is indicated and annotated (524p) on user interface 502.

User interface 502 may further include a selectable UI button 524s to allow the user (e.g., the user of image 202a) to select for purchase or shipment the corresponding product (e.g., manufactured product 524r). In some embodiments, selection of selectable UI button 524s may cause the recommended product(s) to be shipped to the user (e.g., user 202au) and/or may notify a third party that the individual is interested in the product(s). For example, either user computing device 111c1 and/or imaging server(s) 102 may initiate, based on the user-specific scalp classification 510 and/or the user-specific scalp recommendation 512, the manufactured product 524r (e.g., mild shampoo) for shipment to the user. In such embodiments, the product may be packaged and shipped to the user.

In various embodiments, a graphical representation (e.g., image 202a), with graphical annotations (e.g., area of pixel data 202ap), textual annotations (e.g., text 202at), and the user-specific scalp classification 510 and the user-specific scalp recommendation 512 may be transmitted, via the computer network (e.g., from an imaging server 102 and/or one or more processors) to user computing device 111c1, for rendering on display screen 500. In other embodiments, no transmission to the imaging server of the user's specific image occurs, where the user-specific scalp classification 510 and the user-specific scalp recommendation 512 (and/or product specific recommendation) may instead be generated locally, by the scalp based learning model (e.g., scalp based learning model 108) executing and/or implemented on the user's mobile device (e.g., user computing device 111c1) and rendered, by a processor of the mobile device, on display screen 500 of the mobile device (e.g., user computing device 111c1).

In some embodiments, any one or more of graphical representations (e.g., image 202a), with graphical annotations (e.g., area of pixel data 202ap), textual annotations (e.g., text 202at), user-specific scalp classification 510, user-specific scalp recommendation 512, and/or product recommendation 522 may be rendered (e.g., rendered locally on display screen 500) in real-time or near-real time during or after receiving, the image having the scalp region of the user's scalp. In embodiments where the image is analyzed by imaging server(s) 102, the image may be transmitted and analyzed in real-time or near real-time by imaging server(s) 102.

In some embodiments, the user may provide a new image that may be transmitted to imaging server(s) 102 for updating, retraining, or reanalyzing by scalp based learning model 108. In other embodiments, a new image that may be locally received on computing device 111c1 and analyzed, by scalp based learning model 108, on the computing device 111c1.

In addition, as shown in the example of FIG. 5, the user may select selectable button 512i for reanalyzing (e.g., either locally at computing device 111c1 or remotely at imaging server(s) 102) a new image. Selectable button 512i may cause user interface 502 to prompt the user to attach for analyzing a new image. Imaging server(s) 102 and/or a user computing device such as user computing device 111c1 may receive a new image comprising pixel data of at least a portion of a scalp region of the user's scalp. The new image may be captured by the imaging device. The new image (e.g., similar to image 202a) may comprise pixel data of at least a portion of a scalp region of the user's scalp. The scalp based learning model (e.g., scalp based learning model 108), executing on the memory of the computing device (e.g., imaging server(s) 102), may analyze the new image captured by the imaging device to determine an image classification of the user's scalp region. The computing device (e.g., imaging server(s) 102) may generate, based on a comparison of the image and the second image or the classification and the second classification of the user's scalp region, a new user-specific scalp classification and/or a new user-specific scalp recommendation regarding at least one feature identifiable within the pixel data of the new image. For example, the new user-specific scalp classification may include a new graphical representation including graphics and/or text (e.g., showing a new scalp quality score value, e.g., 1, after the user washed their hair). The new user-specific scalp classification may include additional scalp classifications, e.g., that the user has successfully washed their hair to reduce white residue and/or scalp acne as detected with the pixel data of the new image. A comment may include that the user needs to correct additional features detected within the pixel data, e.g., scalp lines/cracks, by applying an additional product, e.g., moisturizing shampoo or coconut oil.

In various embodiments, the new user-specific scalp classification and/or the new user-specific scalp recommendation may be transmitted via the computer network, from server(s) 102, to the user computing device of the user for rendering on the display screen 500 of the user computing device (e.g., user computing device 111c1).

In other embodiments, no transmission to the imaging server of the user's new image occurs, where the new user-specific scalp classification and/or the new user-specific scalp recommendation (and/or product specific recommendation) may instead be generated locally, by the scalp based learning model (e.g., scalp based learning model 108)

executing and/or implemented on the user's mobile device (e.g., user computing device 111c1) and rendered, by a processor of the mobile device, on a display screen of the mobile device (e.g., user computing device 111c1).

Aspects of the Disclosure

The following aspects are provided as examples in accordance with the disclosure herein and are not intended to limit the scope of the disclosure.

1. A digital imaging and learning system configured to analyze pixel data of an image of a scalp region of a user's scalp to generate one or more user-specific scalp classifications, the digital imaging and learning system comprising: one or more processors; an imaging application (app) comprising computing instructions configured to execute on the one or more processors; and a scalp based learning model, accessible by the imaging app, and trained with pixel data of a plurality of training images depicting scalp regions of scalps of respective individuals, the scalp based learning model configured to output one or more image classifications corresponding to one or more features of scalp skin or hair follicle regions of the respective individuals, wherein the computing instructions of the imaging app when executed by the one or more processors, cause the one or more processors to: receive an image of a user, the image comprising a digital image as captured by an imaging device, and the image comprising pixel data of at least a portion of a scalp region of the user's scalp, analyze, by the scalp based learning model, the image as captured by the imaging device to determine at least one image classification of the user's scalp region, the at least one image classification selected from the one or more image classifications of the scalp based learning model, and generate, based on the at least one image classification of the user's scalp region, a user-specific scalp classification designed to address at least one feature identifiable within the pixel data comprising the at least the portion of a scalp region of the user's scalp.

2. The digital imaging and learning system of aspect 1, wherein the one or more image classifications comprise one or more of: (1) a white residue image classification; (2) a scalp plug image classification; or (3) a scalp acne image classification.

3. The digital imaging and learning system of any one of aspects 1-2, wherein the computing instructions further cause the one or more processors to: analyze, by the scalp based learning model, the image captured by the imaging device to determine a second image classification of the user's scalp region as selected from the one or more image classifications of the scalp based learning model, wherein the user-specific scalp classification is further based on the second image classification of the user's scalp region.

4. The digital imaging and learning system of any one of aspects 1-3, wherein the scalp region of the user comprises scalp skin having one or more scalp skin features identifiable within the pixel data, the one or more scalp skin features comprising one or more of: (1) white sebum residue; (2) one or more lines of the scalp skin; or (3) one or more cracks of the scalp skin.

5. The digital imaging and learning system of any one of aspects 1-4, wherein the scalp region of the user comprises hair follicle regions having one or more hair follicle features identifiable within the pixel data, the one or more hair follicle features comprising one or more of: (1) one or more scalp plugs; or (2) scalp acne.

6. The digital imaging and learning system of any one of aspects 1-5, wherein the scalp region of the user comprises at least one of: a frontal scalp region, a mid-center scalp region, or a custom defined scalp region.

7. The digital imaging and learning system of any one of aspects 1-6, wherein one or more of the plurality of training images or the at least one image of the user each comprise at least one cropped image depicting the scalp region having a single instance of a scalp skin feature or a hair follicle feature.

8. The digital imaging and learning system of any one of aspects 1-7, wherein one or more of the plurality of training images or the at least one image of the user comprise multiple angles or perspectives depicting scalp regions of the respective individuals or the user.

9. The digital imaging and learning system of any one of aspects 1-8, wherein the computing instructions of the imaging app when executed by the one or more processors, further cause the one or more processors to: render, on a display screen of a computing device, at least one user-specific scalp recommendation based on the user-specific scalp classification.

10. The digital imaging and learning system of aspect 9, wherein the at least one user-specific scalp recommendation is displayed on the display screen of the computing device with instructions for treating the at least one feature identifiable in the pixel data comprising the at least the portion of the scalp region of the user's scalp.

11. The digital imaging and learning system of any one of aspects 9-10, wherein the at least one user-specific scalp recommendation comprises a recommended wash frequency specific to the user.

12. The digital imaging and learning system of any one of aspects 9-11, wherein the at least one user-specific scalp recommendation comprises a textual recommendation, an imaged based recommendation, or virtual rendering of the at least the portion of the scalp region of the user's scalp.

13. The digital imaging and learning system of any one of aspects 9-12, wherein the at least one user-specific scalp recommendation comprises is rendered on the display screen in real-time or near-real time, during, or after receiving, the image having the scalp region of the user's scalp.

14. The digital imaging and learning system of any one of aspects 9-13, wherein the at least one user-specific scalp recommendation comprises a product recommendation for a manufactured product.

15. The digital imaging and learning system of aspect 14, wherein the at least one user-specific scalp recommendation is displayed on the display screen of the computing device with instructions for treating, with the manufactured product, the at least one feature identifiable in the pixel data comprising the at least the portion of a scalp region of the user's scalp.

16. The digital imaging and learning system of any one of aspects 14-15, wherein the computing instructions further cause the one or more processors to: initiate, based on the at least one user-specific scalp recommendation, the manufactured product for shipment to the user.

17. The digital imaging and learning system of any one of aspects 14-16, wherein the computing instructions further cause the one or more processors to: generate a modified image based on the image, the modified image depicting how the user's scalp skin or hair follicle regions are predicted to appear after treating the at least one feature with the manufactured product; and render, on the display screen of the computing device, the modified image.

18. The digital imaging and learning system of any one of aspects 1-17, wherein the computing instructions of the imaging app when executed by the one or more processors, further cause the one or more processors to: generate a scalp quality code as determined based on the user-specific scalp classification designed to address the at least one feature identifiable within the pixel data comprising the at least the portion of a scalp region of the user's scalp.

19. The digital imaging and learning system of any one of aspects 1-18, wherein the computing instructions further cause the one or more processors to: record, in one or more memories communicatively coupled to the one or more processors, the image of the user as captured by the imaging device at a first time for tracking changes to user's scalp region over time, receive a second image of the user, the second image captured by the imaging device at a second time, and the second image comprising pixel data of at least a portion of a scalp region of the user's scalp, analyze, by the scalp based learning model, the second image captured by the imaging device to determine, at the second time, a second image classification of the user's scalp region as selected from the one or more image classifications of the scalp based learning model, and generate, based on a comparison of the image and the second image or the classification or the second classification of the user's scalp region, a new user-specific scalp classification regarding at least one feature identifiable within the pixel data of the second image comprising the at least the portion of a scalp region of the user's scalp.

20. The digital imaging and learning system of any one of aspects 1-19, wherein the scalp based learning model is an artificial intelligence (AI) based model trained with at least one AI algorithm.

21. The digital imaging and learning system of aspect 20, wherein the one or more features of scalp skin or hair follicle regions of the plurality of training images differ based one or more user demographics or ethnicities of the respective individuals, and wherein the user-specific scalp classification of the user is generated, by the scalp based learning model, based on an ethnicity or demographic value of the user.

22. The digital imaging and learning system of any one of aspects 1-21, wherein at least one of the one or more processors comprises a processor of a mobile device, and wherein the imaging device comprises a digital camera of the mobile device.

23. The digital imaging and learning system of aspect 22, wherein the mobile device comprises at least one of a handheld device or a portable microscope.

24. The digital imaging and learning system of any one of aspects 1-23, wherein the one or more processors comprises a server processor of a server, wherein the server is communicatively coupled to a computing device via a computer network, and where the imaging app comprises a server app portion configured to execute on the one or more processors of the server and a computing device app portion configured to execute on one or more processors of the computing device, the server app portion configured to communicate with the computing device app portion, wherein the server app portion is configured to implement one or more of: (1) receiving the image captured by the imaging device; (2); determining the at least one image classification of the user's scalp region; (3) generating the user-specific scalp classification; or (4) transmitting a user-specific recommendation the computing device app portion.

25. A digital imaging and learning method for analyzing pixel data of an image of a scalp region of a user's scalp to generate one or more user-specific scalp classifications, the digital imaging and learning method comprising: receiving, at an imaging application (app) executing on one or more processors, an image of a user, the image comprising a digital image as captured by an imaging device, and the image comprising pixel data of at least a portion of a scalp region of the user's scalp; analyzing, by a scalp based learning model accessible by the imaging app, the image as captured by the imaging device to determine at least one image classification of the user's scalp region, the at least one image classification selected from one or more image classifications of the scalp based learning model, wherein the scalp based learning model is trained with pixel data of a plurality of training images depicting scalp regions of scalps of respective individuals, the scalp based learning model operable to output the one or more image classifications corresponding to one or more features of scalp skin or hair follicle regions of the respective individuals; and generating, by the imaging app based on the at least one image classification of the user's scalp region, a user-specific scalp classification designed to address at least one feature identifiable within the pixel data comprising the at least the portion of a scalp region of the user's scalp.

26. The digital imaging and learning method of aspect 25, wherein the one or more image classifications comprise one or more of: (1) a white residue image classification; (2) a scalp plug image classification; or (3) a scalp acne image classification.

27. The digital imaging and learning method of any one of aspects 25-26, wherein the method further comprises: analyzing, by the scalp based learning model, the image captured by the imaging device to determine a second image classification of the user's scalp region as selected from the one or more image classifications of the scalp based learning model, wherein the user-specific scalp classification is further based on the second image classification of the user's scalp region.

28. The digital imaging and learning method of any one of aspects 25-27, wherein the scalp region of the user comprises scalp skin having one or more scalp skin features identifiable within the pixel data, the one or more scalp skin features comprising one or more of: (1) white sebum residue; (2) one or more lines of the scalp skin; or (3) one or more cracks of the scalp skin.

29. The digital imaging and learning method of any one of aspects 25-28, wherein the scalp region of the user comprises hair follicle regions having one or more hair follicle features identifiable within the pixel data, the one or more hair follicle features comprising one or more of: (1) one or more scalp plugs; or (2) scalp acne.

30. The digital imaging and learning method of any one of aspects 25-29, wherein the scalp region of the user comprises at least one of: a frontal scalp region, a mid-center scalp region, or a custom defined scalp region.

31. A tangible, non-transitory computer-readable medium storing instructions for analyzing pixel data of an image of a scalp region of a user's scalp to generate one or more user-specific scalp classifications, that when executed by one or more processors cause the one or more processors to: receive, at an imaging application (app) executing on one or more processors, an image of a user, the image comprising a digital image as captured by an imaging device, and the image comprising pixel data of at least a portion of a scalp region of the user's scalp; analyze, by a scalp based learning model accessible by the imaging app, the image as captured by the imaging device to determine at least one image classification of the user's scalp region, the at least one image classification selected from one or more image classifications of the scalp based learning model, wherein the scalp based learning model is trained with pixel data of a plurality of training images depicting scalp regions of scalps of respective individuals, the scalp based learning model operable to output the one or more image classifications corresponding to one or more features of scalp skin or hair follicle regions of the respective individuals; and generate, by the imaging app based on the at least one image classification of the user's scalp region, a user-specific scalp classification designed to address at least one feature identifiable within the pixel data comprising the at least the portion of a scalp region of the user's scalp.

Additional Considerations

Although the disclosure herein sets forth a detailed description of numerous different embodiments, it should be understood that the legal scope of the description is defined by the words of the claims set forth at the end of this patent and equivalents. The detailed description is to be construed as exemplary only and does not describe every possible embodiment since describing every possible embodiment would be impractical. Numerous alternative embodiments may be implemented, using either current technology or technology developed after the filing date of this patent, which would still fall within the scope of the claims.

The following additional considerations apply to the foregoing discussion. Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location, while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other embodiments, the one or more processors or processor-implemented modules may be distributed across a number of geographic locations.

This detailed description is to be construed as exemplary only and does not describe every possible embodiment, as describing every possible embodiment would be impractical, if not impossible. A person of ordinary skill in the art may implement numerous alternate embodiments, using either current technology or technology developed after the filing date of this application.

Those of ordinary skill in the art will recognize that a wide variety of modifications, alterations, and combinations can be made with respect to the above described embodiments without departing from the scope of the invention, and that such modifications, alterations, and combinations are to be viewed as being within the ambit of the inventive concept.

The patent claims at the end of this patent application are not intended to be construed under 35 U.S.C. § 112(f) unless traditional means-plus-function language is expressly recited, such as "means for" or "step for" language being explicitly recited in the claim(s). The systems and methods described herein are directed to an improvement to computer functionality, and improve the functioning of conventional computers.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A digital imaging and learning system configured to analyze pixel data of an image of a scalp region of a user's scalp to generate one or more user-specific scalp classifications, the digital imaging and learning system comprising:

one or more processors;
an imaging application (app) comprising computing instructions configured to execute on the one or more processors; and
a scalp based learning model, accessible by the imaging app, and trained with pixel data of a plurality of training images depicting scalp regions of scalps of respective individuals, the scalp based learning model configured to output one or more image classifications corresponding to one or more features of scalp skin or hair follicle regions of the respective individuals,
wherein the computing instructions of the imaging app when executed by the one or more processors, cause the one or more processors to:
receive an image of a user, the image comprising a digital image as captured by an imaging device, and the image comprising pixel data of at least a portion of a scalp region of the user's scalp,
analyze, by the scalp based learning model, the image as captured by the imaging device to determine at least one image classification of the user's scalp region, the at least one image classification selected from the one or more image classifications of the scalp based learning model,
generate, based on the at least one image classification of the user's scalp region, a user-specific scalp classification designed to address at least one feature identifiable within the pixel data comprising the at least the portion of a scalp region of the user's scalp;
render, on a display screen of a computing device, at least one user-specific scalp recommendation based on the user-specific scalp classification, wherein the at least one user-specific scalp recommendation comprises a product recommendation for a manufactured product;
generate, based on the image, a modified image, wherein the modified image depicts how the user's scalp skin or hair follicle regions are predicted to appear after treating the at least one feature with the manufactured product; and
render, on the display screen of the computing device, the modified image.

2. The digital imaging and learning system of claim 1, wherein the one or more image classifications comprise one or more of: (1) a white residue image classification; (2) a scalp plug image classification; or (3) a scalp acne image classification.

3. The digital imaging and learning system of claim 1, wherein the computing
instructions further cause the one or more processors to:
analyze, by the scalp based learning model, the image captured by the imaging device to determine a second image classification of the user's scalp region as selected from the one or more image classifications of the scalp based learning model,
wherein the user-specific scalp classification is further based on the second image classification of the user's scalp region.

4. The digital imaging and learning system of claim 1, wherein the scalp region of the user comprises scalp skin having one or more scalp skin features identifiable within the pixel data, the one or more scalp skin features comprising one or more of: (1) white sebum residue; (2) one or more lines of the scalp skin; or (3) one or more cracks of the scalp skin.

5. The digital imaging and learning system of claim 1, wherein the scalp region of the user comprises hair follicle regions having one or more hair follicle features identifiable within the pixel data, the one or more hair follicle features comprising one or more of: (1) one or more scalp plugs; or (2) scalp acne.

6. The digital imaging and learning system of claim 1, wherein the scalp region of the user comprises at least one of: a frontal scalp region, a mid-center scalp region, or a custom defined scalp region.

7. The digital imaging and learning system of claim 1, wherein one or more of the plurality of training images or the at least one image of the user each comprise at least one cropped image depicting the scalp region having a single instance of a scalp skin feature or a hair follicle feature.

8. The digital imaging and learning system of claim 1, wherein one or more of the plurality of training images or the at least one image of the user comprise multiple angles or perspectives depicting scalp regions of the respective individuals or the user.

9. The digital imaging and learning system of claim 1, wherein the at least one user-specific scalp recommendation is displayed on the display screen of the computing device with instructions for treating the at least one feature identifiable in the pixel data comprising the at least the portion of the scalp region of the user's scalp.

10. The digital imaging and learning system of claim 1, wherein the at least one user-specific scalp recommendation comprises a recommended wash frequency specific to the user.

11. The digital imaging and learning system of claim 1, wherein the at least one user-specific scalp recommendation comprises a textual recommendation, an imaged based recommendation, or virtual rendering of the at least the portion of the scalp region of the user's scalp.

12. The digital imaging and learning system of claim 1, wherein the at least one user-specific scalp recommendation is rendered on the display screen in real-time or near-real time, during, or after receiving, the image having the scalp region of the user's scalp.

13. The digital imaging and learning system of claim 1, wherein the at least one user-specific scalp recommendation is displayed on the display screen of the computing device with instructions for treating, with the manufactured product, the at least one feature identifiable in the pixel data comprising the at least the portion of a scalp region of the user's scalp.

14. The digital imaging and learning system of claim 1, wherein the computing instructions further cause the one or more processors to:
initiate, based on the at least one user-specific scalp recommendation, the manufactured product for shipment to the user.

15. The digital imaging and learning system of claim 1, wherein the computing instructions of the imaging app when executed by the one or more processors, further cause the one or more processors to:
generate a scalp quality code as determined based on the user-specific scalp classification designed to address the at least one feature identifiable within the pixel data comprising the at least the portion of a scalp region of the user's scalp.

16. The digital imaging and learning system of claim 1, wherein the computing instructions further cause the one or more processors to:
record, in one or more memories communicatively coupled to the one or more processors, the image of the user as captured by the imaging device at a first time for tracking changes to user's scalp region over time, receive a second image of the user, the second image captured by the imaging device at a second time, and the second image comprising pixel data of at least a portion of a scalp region of the user's scalp, analyze, by the scalp based learning model, the second image captured by the imaging device to determine, at the second time, a second image classification of the user's scalp region as selected from the one or more image classifications of the scalp based learning model, and generate, based on a comparison of the image and the second image or the classification or the second classification of the user's scalp region, a new user-specific scalp classification regarding at least one feature identifiable within the pixel data of the second image comprising the at least the portion of a scalp region of the user's scalp.

17. The digital imaging and learning system of claim 1, wherein the scalp based learning model is an artificial intelligence (AI) based model trained with at least one AI algorithm.

18. The digital imaging and learning system of claim 17, wherein the one or more features of scalp skin or hair follicle regions of the plurality of training images differ based one or more user demographics or ethnicities of the respective individuals, and
   wherein the user-specific scalp classification of the user is generated, by the scalp based learning model, based on an ethnicity or demographic value of the user.

19. The digital imaging and learning system of claim 1, wherein at least one of the one or more processors comprises a processor of a mobile device, and wherein the imaging device comprises a digital camera of the mobile device.

20. The digital imaging and learning system of claim 19, wherein the mobile device comprises at least one of a handheld device or a portable microscope.

21. The digital imaging and learning system of claim 1, wherein the one or more processors comprises a server processor of a server, wherein the server is communicatively coupled to a computing device via a computer network, and where the imaging app comprises a server app portion configured to execute on the one or more processors of the server and a computing device app portion configured to execute on one or more processors of the computing device, the server app portion configured to communicate with the computing device app portion, wherein the server app portion is configured to implement one or more of: (1) receiving the image captured by the imaging device; (2); determining the at least one image classification of the user's scalp region; (3) generating the user-specific scalp classification; or (4) transmitting a user-specific recommendation the computing device app portion.

22. A digital imaging and learning method for analyzing pixel data of an image of a scalp region of a user's scalp to generate one or more user-specific scalp classifications, the digital imaging and learning method comprising:
   receiving, at an imaging application (app) executing on one or more processors, an image of a user, the image comprising a digital image as captured by an imaging device, and the image comprising pixel data of at least a portion of a scalp region of the user's scalp;
   analyzing, by a scalp based learning model accessible by the imaging app, the image as captured by the imaging device to determine at least one image classification of the user's scalp region, the at least one image classification selected from one or more image classifications of the scalp based learning model, wherein the scalp based learning model is trained with pixel data of a plurality of training images depicting scalp regions of scalps of respective individuals, the scalp based learning model operable to output the one or more image classifications corresponding to one or more features of scalp skin or hair follicle regions of the respective individuals;
   generating, by the imaging app based on the at least one image classification of the user's scalp region, a user-specific scalp classification designed to address at least one feature identifiable within the pixel data comprising the at least the portion of a scalp region of the user's scalp;
   render, on a display screen of a computing device, at least one user-specific scalp recommendation based on the user-specific scalp classification, wherein the at least one user- specific scalp recommendation comprises a product recommendation for a manufactured product;
   generate, based on the image, a modified image, wherein the modified image depicts how the user's scalp skin or hair follicle regions are predicted to appear after treating the at least one feature with the manufactured product; and
   render, on the display screen of the computing device, the modified image.

23. The digital imaging and learning method of claim 22, wherein the one or more image classifications comprise one or more of: (1) a white residue image classification; (2) a scalp plug image classification; or (3) a scalp acne image classification.

24. The digital imaging and learning method of claim 22, wherein the method further comprises:
   analyzing, by the scalp based learning model, the image captured by the imaging device to determine a second image classification of the user's scalp region as selected from the one or more image classifications of the scalp based learning model,
   wherein the user-specific scalp classification is further based on the second image classification of the user's scalp region.

25. The digital imaging and learning method of claim 22, wherein the scalp region of the user comprises scalp skin having one or more scalp skin features identifiable within the pixel data, the one or more scalp skin features comprising one or more of: (1) white sebum residue; (2) one or more lines of the scalp skin; or (3) one or more cracks of the scalp skin.

26. The digital imaging and learning method of claim 22, wherein the scalp region of the user comprises hair follicle regions having one or more hair follicle features identifiable within the pixel data, the one or more hair follicle features comprising one or more of: (1) one or more scalp plugs; or (2) scalp acne.

27. The digital imaging and learning method of claim 22, wherein the scalp region of the user comprises at least one of: a frontal scalp region, a mid-center scalp region, or a custom defined scalp region.

28. A tangible, non-transitory computer-readable medium storing instructions for analyzing pixel data of an image of a scalp region of a user's scalp to generate one or more user-specific scalp classifications, that when executed by one or more processors cause the one or more processors to:
   receive, at an imaging application (app) executing on one or more processors, an image of a user, the image comprising a digital image as captured by an imaging device, and the image comprising pixel data of at least a portion of a scalp region of the user's scalp;

analyze, by a scalp based learning model accessible by the imaging app, the image as captured by the imaging device to determine at least one image classification of the user's scalp region, the at least one image classification selected from one or more image classifications of the scalp based learning model, wherein the scalp based learning model is trained with pixel data of a plurality of training images depicting scalp regions of scalps of respective individuals, the scalp based learning model operable to output the one or more image classifications corresponding to one or more features of scalp skin or hair follicle regions of the respective individuals; generate, by the imaging app based on the at least one image classification of the user's scalp region, a user-specific scalp classification designed to address at least one feature identifiable within the pixel data comprising the at least the portion of a scalp region of the user's scalp;

render, on a display screen of a computing device, at least one user-specific scalp recommendation based on the user-specific scalp classification, wherein the at least one user-specific scalp recommendation comprises a product recommendation for a manufactured product;

generate, based on the image, a modified image, wherein the modified image depicts how the user's scalp skin or hair follicle regions are predicted to appear after treating the at least one feature with the manufactured product; and render, on the display screen of the computing device, the modified image.

* * * * *